(12) United States Patent
La Lumondiere et al.

(10) Patent No.: US 9,007,454 B2
(45) Date of Patent: Apr. 14, 2015

(54) OPTIMIZED ILLUMINATION FOR IMAGING

(71) Applicant: The Aerospace Corporation, El Segundo, CA (US)

(72) Inventors: Stephen La Lumondiere, Torrance, CA (US); Terence Yeoh, Pasadena, CA (US); David Cardoza, Los Alamitos, CA (US)

(73) Assignee: The Aerospace Corporation, El Segundo, CA (US)

( * ) Notice: Subject to any disclaimer, the term of this patent is extended or adjusted under 35 U.S.C. 154(b) by 254 days.

(21) Appl. No.: 13/665,445

(22) Filed: Oct. 31, 2012

(65) Prior Publication Data

US 2014/0118561 A1    May 1, 2014

(51) Int. Cl.
| | |
|---|---|
| H04N 7/18 | (2006.01) |
| H04N 5/222 | (2006.01) |
| G01N 21/95 | (2006.01) |
| H04N 5/235 | (2006.01) |

(52) U.S. Cl.
CPC ......... H04N 5/2354 (2013.01); G01N 21/9505 (2013.01)

(58) Field of Classification Search
CPC .......... G01N 21/9501; G01N 21/9505; G01N 21/95; G01N 21/8806; G01N 21/958
USPC ............................................ 348/87, 370, 371
See application file for complete search history.

(56) References Cited

U.S. PATENT DOCUMENTS

| | | |
|---|---|---|
| 5,131,963 A | 7/1992 | Ravi |
| 5,192,980 A | 3/1993 | Dixon et al. |
| 5,196,716 A | 3/1993 | Moriya et al. |
| 5,220,403 A | 6/1993 | Batchelder et al. |
| 5,754,514 A | 5/1998 | Guerra |
| 5,757,050 A | 5/1998 | Adler et al. |
| 5,900,354 A | 5/1999 | Batchelder et al. |
| 5,930,588 A | 7/1999 | Paniccia |

(Continued)

FOREIGN PATENT DOCUMENTS

| | | |
|---|---|---|
| EP | 0887621 A1 | 12/1998 |
| WO | WO 98/21687 A1 | 5/1998 |

(Continued)

OTHER PUBLICATIONS

International Search Report and Written Opinion of the International Search Authority mailed in Application No. PCT/US2010/046978 on Dec. 17, 2010.

(Continued)

*Primary Examiner* — Timothy J Henn
(74) *Attorney, Agent, or Firm* — K&L Gates LLP

(57) ABSTRACT

Various embodiments are directed to imaging systems and methods for generating an image of a sub-surface feature of an object through a surface of the object. An illumination array may comprise a plurality of illumination sources positioned around the sub-surface feature of the object. An imaging device may comprise an objective. A computer system may be in communication with the illumination array. The computer system may be programmed to calculate an optimized illumination pattern of the plurality of illumination sources for imaging the sub-surface feature; activate the optimized illumination pattern; and instruct the imaging device to capture an image of the sub-surface feature with the imaging device based on reflected illumination from the optimized illumination pattern.

19 Claims, 19 Drawing Sheets

(56) References Cited

U.S. PATENT DOCUMENTS

| | | |
|---|---|---|
| 5,946,543 A | 8/1999 | Kimura et al. |
| 5,966,019 A | 10/1999 | Borden |
| 6,005,965 A | 12/1999 | Tsuda et al. |
| 6,055,055 A | 4/2000 | Toh |
| 6,266,130 B1 | 7/2001 | Hasegawa et al. |
| 6,731,660 B2 | 5/2004 | Arbore et al. |
| 6,734,960 B1 | 5/2004 | Goto et al. |
| 6,859,516 B2 | 2/2005 | Schneider et al. |
| 6,906,801 B2 | 6/2005 | Borden et al. |
| 6,961,124 B2 | 11/2005 | Engelhardt et al. |
| 7,038,208 B2 | 5/2006 | Alfano et al. |
| 7,244,665 B2 | 7/2007 | Benson |
| 7,327,450 B2 | 2/2008 | Kreh et al. |
| 7,470,986 B2 | 12/2008 | Kaneko |
| 7,679,730 B2 | 3/2010 | Takano et al. |
| 7,869,025 B2 | 1/2011 | Soeda et al. |
| 7,890,158 B2 | 2/2011 | Rowe et al. |
| 8,072,007 B2 | 12/2011 | Koshiba |
| 8,077,305 B2 | 12/2011 | Owen et al. |
| 8,138,476 B2 | 3/2012 | La Lumondiere et al. |
| 8,212,215 B2 | 7/2012 | La Lumondiere et al. |
| 8,217,937 B2 | 7/2012 | Yeoh et al. |
| 8,254,020 B2 | 8/2012 | Holy et al. |
| 8,450,688 B2 | 5/2013 | La Lumondiere et al. |
| 8,461,532 B2 | 6/2013 | La Lumondiere et al. |
| 8,520,208 B1* | 8/2013 | Biellak et al. .......... 356/369 |
| 2002/0005493 A1 | 1/2002 | Reese et al. |
| 2002/0111546 A1* | 8/2002 | Cook et al. ............ 600/322 |
| 2007/0253033 A1* | 11/2007 | Johansen et al. ........ 358/448 |
| 2011/0002529 A1* | 1/2011 | Jeong et al. ............ 382/147 |
| 2011/0102615 A1* | 5/2011 | La Lumondiere et al. 348/222.1 |
| 2011/0102770 A1* | 5/2011 | La Lumondiere et al. ..... 356/51 |
| 2011/0149062 A1* | 6/2011 | Campidell et al. ............ 348/87 |
| 2012/0019707 A1* | 1/2012 | La Lumondiere et al. ... 348/342 |
| 2013/0010175 A1* | 1/2013 | Pichon et al. ............ 348/335 |
| 2013/0278749 A1* | 10/2013 | Mandelis et al. ............ 348/87 |

FOREIGN PATENT DOCUMENTS

| | | | |
|---|---|---|---|
| WO | WO 2008/119550 A1 | 10/2008 | |
| WO | WO 2008/120883 A1 | 10/2008 | |

OTHER PUBLICATIONS

International Search Report and Written Opinion of the International Search Authority mailed in Application No. PCT/US2011/028514 on Jun. 24, 2011.

Vasefi et al., "An Optical Imaging Technique Using Deep Illumination in the Angular Domain," 2007, IEEE Journal of Selected Topics in Quantum Electronics, vol. 13, No. 6, pp. 1610-1620.

Springholz, G., "Strain contrast in scanning tunneling microscopy imaging of subsurface feature dislocations in lattice-mismatched heteoepitaxy", 1997, Applied Surface Science, vol. 112, pp. 12-22.

Ramsay et al., "Three-dimensional nanometric sub-surface imaging of a silicon flip-chip using the two-photon optical beam induced current method", 2007, Microelectronics Reliability, vol. 47, pp. 1534-1538.

Pfister et al., "Surface and subsurface imaging of indium in InGaAs by scanning tunneling microscopy", 1996, Applied Surface Science, vol. 104/105, pp. 516-521.

\* cited by examiner

OPTIMIZED ILLUMINATION FOR IMAGING

BACKGROUND

In semiconductor fabrication and other fields, it is often necessary or desirable to image subsurface objects. For example, when a semiconductor chip is constructed according to "flip-chip" mounting techniques, component structures on the chip are obscured by the substrate. Various semiconductor fabrication and testing techniques require high-contrast imaging of components. Some examples of these techniques include Laser Assisted Chemical Etching, Focused Ion Beam, and others. Imaging through common substrate materials, such as silicon, is possible, although, difficulties exist.

One method of imaging through substrate material is conventional bright field microscopy. According to bright field microscopy, illumination is provided in a direction normal to the substrate surface. An image is captured with a camera or other imaging device also oriented normal to the substrate surface. While this technique can be relatively inexpensive, the resolution of the resulting images is often disappointing. This is, at least in part, because backscatter off of the substrate is directed back towards, and captured by, the objective lens of the imaging device. This has the effect of blurring and washing out the resulting image. It is known to enhance the resolution of bright field microscopy by applying an anti-reflective coating to the substrate. This method, however, is expensive and requires that the target semiconductor chip be subjected to one or more additional processing steps. It is also known to use laser scanning confocal microscopy to achieve higher resolution images through semiconductor substrates. Although laser scanning confocal microscopy does produce good results, the equipment for implementing it is extremely expensive, limiting its practical usefulness.

FIGURES

Various embodiments of the present invention are described here by way of example in conjunction with the following figures, wherein:

FIG. 7 illustrates one embodiment of the object of FIG. 1 showing two subsurface features and the ray reflections there from.

FIG. 18a illustrates an image that may be imaged by the system of FIG. 12.

FIG. 18b illustrates a region-of-interest (ROI) selected from the image of FIG. 18a.

FIG. 19a illustrates the ROI of FIG. 18a indicating an example lineout.

FIG. 19b illustrates an intensity plot of the horizontal lineout of FIG. 19a.

DESCRIPTION

Figure 1:
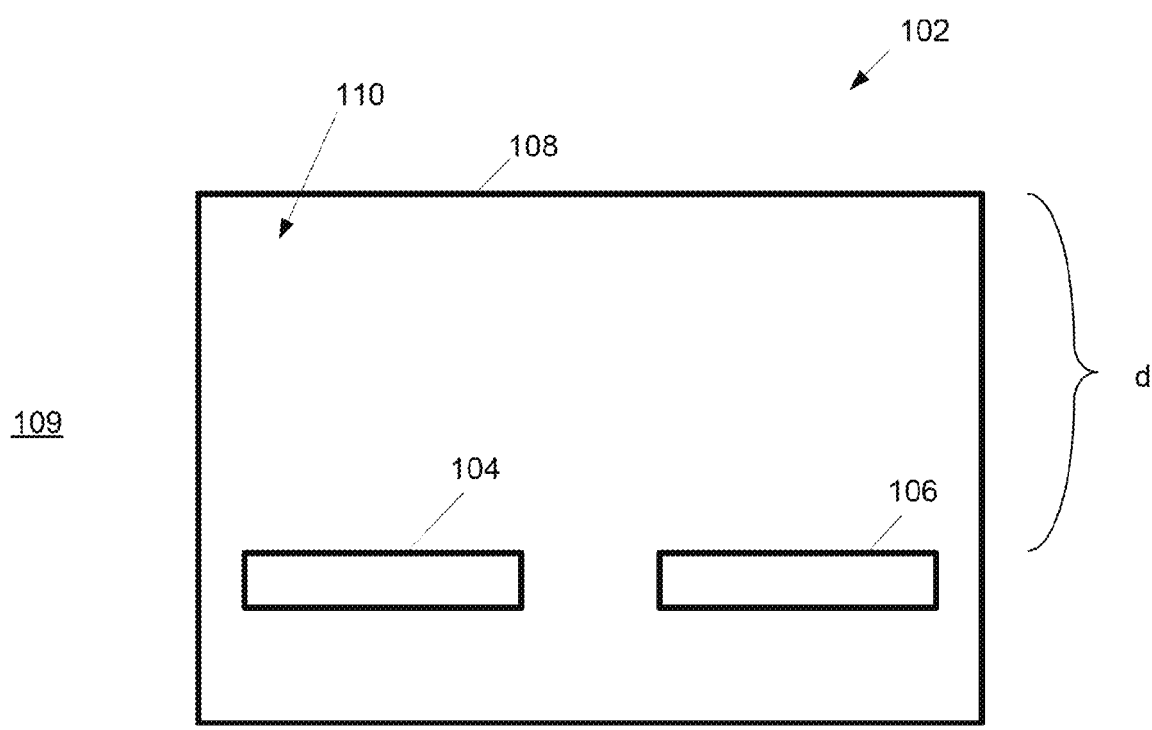
FIG. 1 illustrates a cross-sectional view of one embodiment of an object having subsurface features that may be imaged utilizing the side-addressed illumination techniques described herein.

Various embodiments are directed to systems and methods for optimizing illumination for imaging, including for side-addressed imaging, as described herein. Images of an object may have different qualities depending on the lighting or illumination conditions that are present. Example illumination conditions include, for example, the number of illumination sources present, the direction from which the illumination source is directed to the object, the intensity of illumination received from the illumination source, etc. The optimal illumination conditions for any given object may comprise different combinations of the example illumination conditions described herein.

In various embodiments, an illumination array comprises a plurality of illumination sources. Each illumination source may be directed to the object from a different direction. In some embodiments, different illumination sources are directed to the object from different angles relative to a normal of the object surface. The illumination array may be configurable to provide a plurality of different illumination patterns. For each distinct illumination pattern, a set of sources from the illumination array are illuminated. In some embodiments, an illumination pattern may also specify an intensity of illumination from each illumination source. For example, multiple illumination patterns may involve illumination of the same illumination sources, albeit at different combinations of intensities.

A computer or other processing device may be utilized to determine an optimal illumination pattern for an object. Optimal illumination patterns may be selected by applying an optimization algorithm to a set of illumination patterns that are capable of being provided by the illumination array. An optimization algorithm may be applied to determine one or more illumination patterns generating the highest quality image, referred to herein as optimal illumination patterns. Subsequent images of the object may be captured utilizing the one or more optimal illumination patterns. The quality of images resulting from any particular illumination pattern may be measured in any suitable manner. In some embodiments, image quality may be measured by contrast. For example, images of an object exhibiting relatively higher contrast may be considered superior to images exhibiting lesser contrast.

Any suitable optimization algorithm may be used to generate optimal illumination patterns. For example, in some embodiments, a set of potential illumination patterns is generated and/or received by a computer or other processing device. The computer may instruct the imaging device and/or illumination array to capture images of the object with each of the set of potential illumination patterns activated by the illumination array. The resulting images may be evaluated using a fitness function to determine a quality of each image. The quality of each image may be utilized to generate a fitness function value of the corresponding illumination pattern. Based on the fitness function values for each illumination pattern, a new set of potential illumination patterns may be generated. New fitness function values for the new illumination values may be determined, as described. Additional sets of potential illumination values may be generated in the manner described. Continued iterations may be performed until one or more optimal illumination patterns are converged upon by the algorithm. Example optimization algorithms that may be used to determine the optimal illumination pattern or patterns include global search algorithms (GSA's) such as evolutionary algorithms (e.g., genetic algorithms, evolutionary programming, gene expression algorithms, evolution strategy, differential evolution, neuroevolution, learning classifier algorithms, etc.) and swarm intelligence algorithms (e.g., ant colony optimization, bees algorithm, cuckoo search, particle swarm optimization, firefly algorithm, invasive weed algorithm, harmony search, Gaussian adaptation, etc.).

The illumination optimization systems and methods described herein may be utilized in any type of imaging including, for example, bright-field microscopy, laser scanning confocal microscopy, side-addressed illumination imaging, etc. Examples of side-addressed illumination imaging that may be utilized in conjunction with the illumination optimization described herein are provided in the following commonly-owned United States patents and applications, which are incorporated herein by reference in their entireties: (1) U.S. Pat. No. 8,138,476 to La Lumondiere, et al., issued on Mar. 20, 2012; (2) U.S. Pat. No. 8,212,215 to La Lumondiere, et al., issued on Jul. 3, 2012; (3) U.S. Patent Application Publication No. 2011/0102615 by La Lumondiere, et al., filed on Mar. 26, 2010; and (4) U.S. Patent Application Publication No. 2012/0019707 by La Lumondiere, et al., filed on Jul. 25, 2011.

FIGS. 1-7 provide a description of the operation of side-addressed illumination. It will be appreciated, however, that the illumination optimization techniques described herein may be used with other imaging techniques as well. FIG. 1 illustrates a cross-sectional view of one embodiment of an object 102 having an outer surface 108 and subsurface features 104, 106 that may be imaged utilizing the side-addressed illumination techniques described herein. The material 110 of the object 102 between the subsurface features 104, 106 and the surface 108 may have an index of refraction at the imaging wavelength range that is greater than that of the surrounding medium 109, which may be air. The techniques and apparatuses described herein may be used to image subsurface features in many contexts. In various embodiments, however, the object 102 may comprise a semiconductor substrate and the features 104, 106 may be components such as transistors, diodes, resistors, metallization lines and/or other components formed from or on the substrate of the object 102. In this case, the imaging wavelength range may comprise some or all of the near infrared range, which is transparent in silicon. The ratio of the indices of refraction of the material 110 over the surrounding medium 109 (e.g. air) may be approximately 3.5.

It will be appreciated that, when the object 102 is a semiconductor device, the material 110 may be any suitable semiconductor material including, for example, silicon, gallium arsenide (GaAs), silicon carbide (SiC), and/or diamond. In some embodiments, the object 102 may be mounted in a flip-chip manner. Accordingly, the features 104, 106 may be visible through the remainder of the object 102 (e.g., the substrate). As viewed through the material 110, the features 104, 106 may be below the surface of the object 102 by any suitable distance d that permits transmission of illumination from an illumination source and reformation of an image by the objective or the objective lens of an imaging device (see FIG. 2). In some embodiments, the distance d may be 700 microns.

Figure 2:
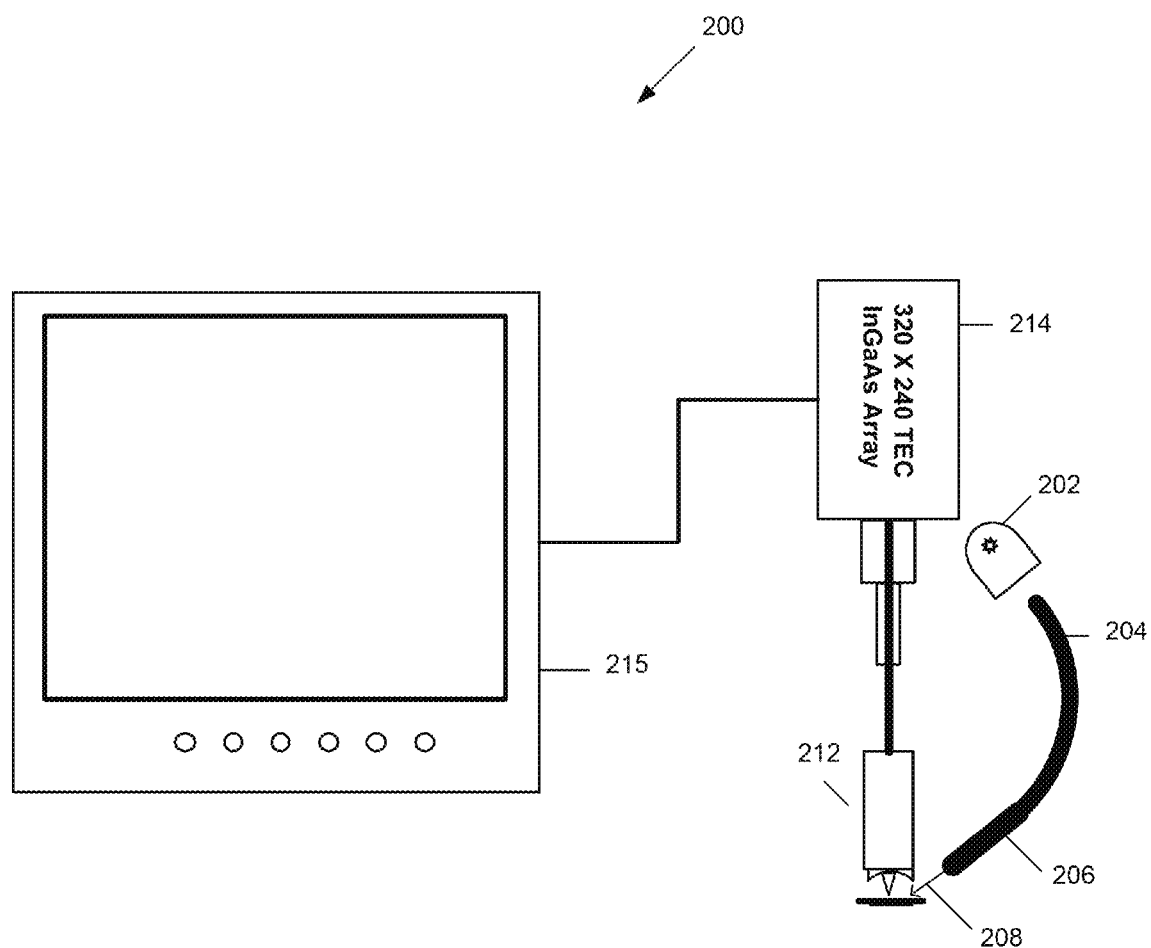
FIG. 2 illustrates one embodiment of a system for side-addressed imaging.

FIG. 2 illustrates one embodiment of a system 200 for side-addressed imaging. The system 200 includes an illumination source 202 optically coupled to a fiber optic bundle 204 (e.g., made of quartz or other suitable material) and a collimating lens 206. According to various embodiments, the source 202 may comprise a tungsten halogen lamp with a gold-plated reflector. It will be appreciated that suitable systems may omit various components such as the fiber optic bundle 204 and collimating lens and/or incorporate some or all of these components into the illumination source 202 itself. Light emitted by the source 202 may be incident on, and may traverse, the fiber optic bundle 204 and collimating lens 206 resulting in a beam 208 incident on the object 102 at an angle offset from the surface normal. Although the source 202 is illustrated as emitting a collimated beam, it will be appreciated that an uncollimated source may be used as well. An objective lens or objective 212 may be positioned approximately along a normal of the object 102 and may direct reflected portions of the beam 208 towards an imaging device 214. The objective 212 may comprise a lens or combination of lenses and/or apertures. The lens or lenses of the objective 212 may comprise a standard lens or, in various embodiments, may comprise a confocal lens for generating three dimensional images. According to various embodiments, the objective 212 may comprise a 1× relay optic and a an NIR 50× long working distance objective, available from MITUTOYO.

The imaging device 214 may comprise any suitable camera or other imaging element capable of sensing the imaging wavelength range. For example, as shown, the imaging device 214 may comprise a 320×240 Indium Gallium Arsenide (InGaAs) array, such as a GOODRICH SU320 sensor with 25 µm pixel pitch. The combination of the MITUTOYO NIR 50× objective 212 and the GOODRICH SU320 sensor may yield a field-of-view of 300 µm×200 µm. It will be appreciated, however, that different sensor sizes and objective components may be used to generate any suitable field of view. The imaging device 214 may capture an image and display it on a monitor 215 or similar visual display device. In addition to, or instead of, displaying the image on the monitor 215, the imaging device 214 may store captured images at a computer readable medium (not shown), such as read only memory (ROM), random access memory (RAM), a hard drive, a flash drive or other data storage device.

According to various embodiments the system 200 may utilize an imaging wavelength or wavelength range that is transparent, or near-transparent, relative to the material 110. For example, when backside imaging is performed through a silicon substrate, the imaging wavelength range may be selected to include wavelengths greater than about 1100 nm. The imaging wavelength range may be implemented in any suitable way. For example, the source 202 may be a broadband source and one or more optical filters may be positioned in the optical path between the source 202 and the imaging device 214. Also, for example, the source 202 may be a narrow-band source that emits only radiation in the imaging wavelength range. In addition to, or instead of these variations, the imaging device 214 may be a narrow band device that is sensitive only to radiation in the imaging wavelength range (e.g., an InGaAs imaging device 214 may be selected with a sensitivity between 900 nm and 1700 nm). In some embodiments, the object 102 may serve as an optical filter. For example, when the object 102 is a silicon substrate and the illumination source 202 is a broadband source, the silicon substrate may tend to absorb all wavelengths other than the near-infrared wavelengths, which are reflected and refracted as described herein.

Figure 3:
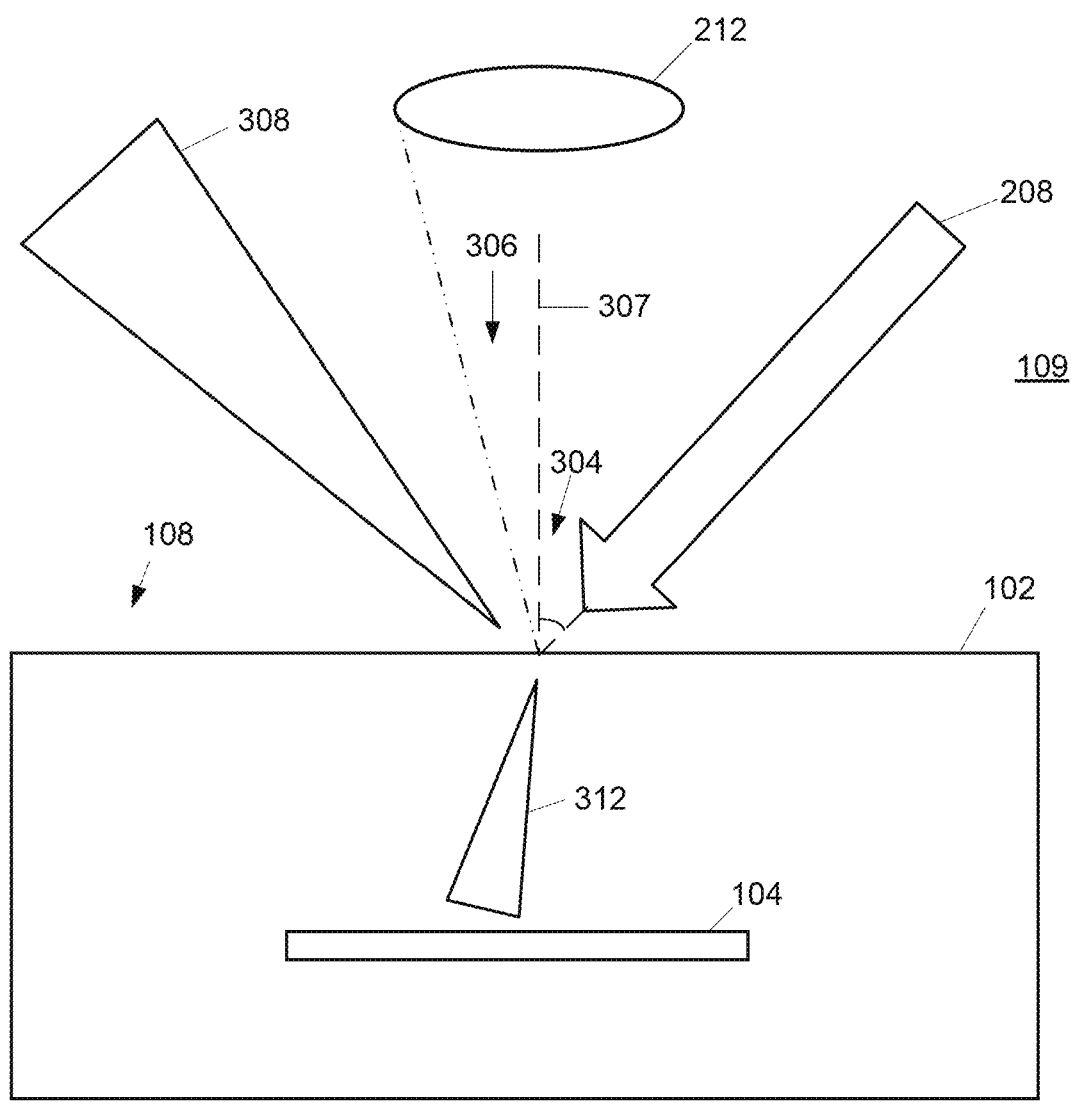
FIG. 3 illustrates one embodiment of the object of FIG. 1 illuminated by an illumination beam.

FIG. 3 illustrates one embodiment of the object 102 showing subsurface feature 104. The incident beam 208 is incident on the object 102 at an angle 304 relative to the surface normal 307. The angle 304 may be set based on the position and orientation of the illumination source 202. The angle 304 may be selected such that specular reflection of the beam 208 off of the object 102 falls outside of an acceptance angle 306 of the objective 212. For example, the angle 304 may be at least equal to the acceptance angle 306 of the objective 212 and less than 90°. It will be appreciated that as the angle 304 increases, the intensity of the light source 202 may also need to be increased to compensate for increasing portions of the illumination beam 208 being reflected off of the object 102 out of the view of the objective 212.

In practice, reflection from the object 102 may not be perfectly specular (e.g., the surface 108 may not be perfectly smooth). Accordingly, the beam 208 may scatter off of the object 102 at a range of angles represented by cone 308. To compensate for this effect, the angle 304 may be selected to be slightly larger than the acceptance angle of the objective 212 such that the actual reflection of the beam 208 off of the object 102 falls substantially outside of the acceptance angle 306 of the objective 212. In this way, the image noise due to surface reflection may be minimized. In one example embodiment where the object 102 is a silicon substrate, the angle 304 may be 45°.

A portion of the beam 208 may be transmitted through the interface between the surrounding medium 109 (e.g., air) and the object 102. Due to the differing indices of refraction between the surrounding medium 109 and the material 110, the resulting light will be refracted towards the normal direction. Also, because the surface 108 of the object 102 may not be perfectly smooth, the refracted portion of the beam 208 may begin to spread, as represented by cone 312. The refracted portion 312 may be incident on and illuminate the feature 104 for imaging.

Figure 4:
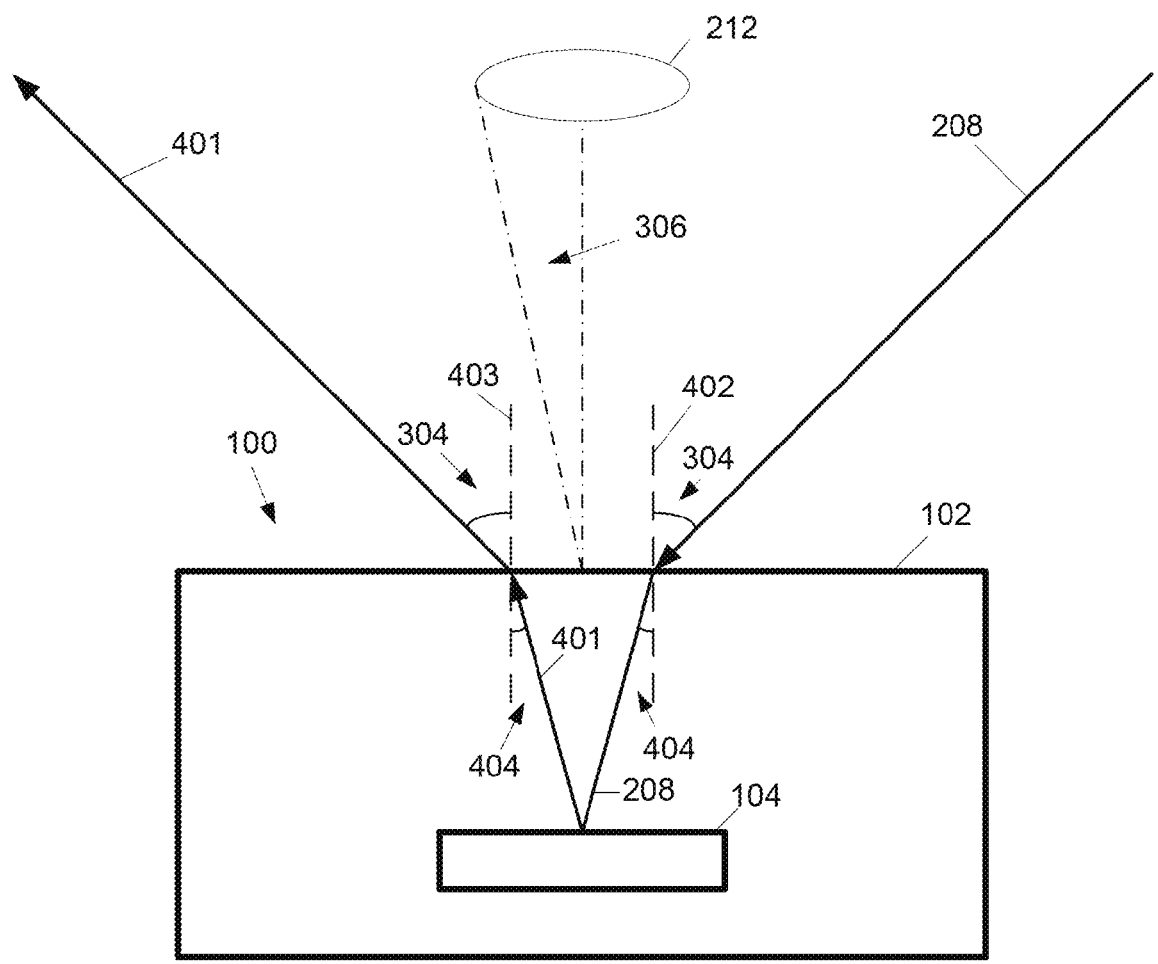
FIG. 4 illustrates one embodiment of the object of FIG. 1 illuminated by the beam oriented at an angle relative to normal of the surface of the object.
Figure 5:
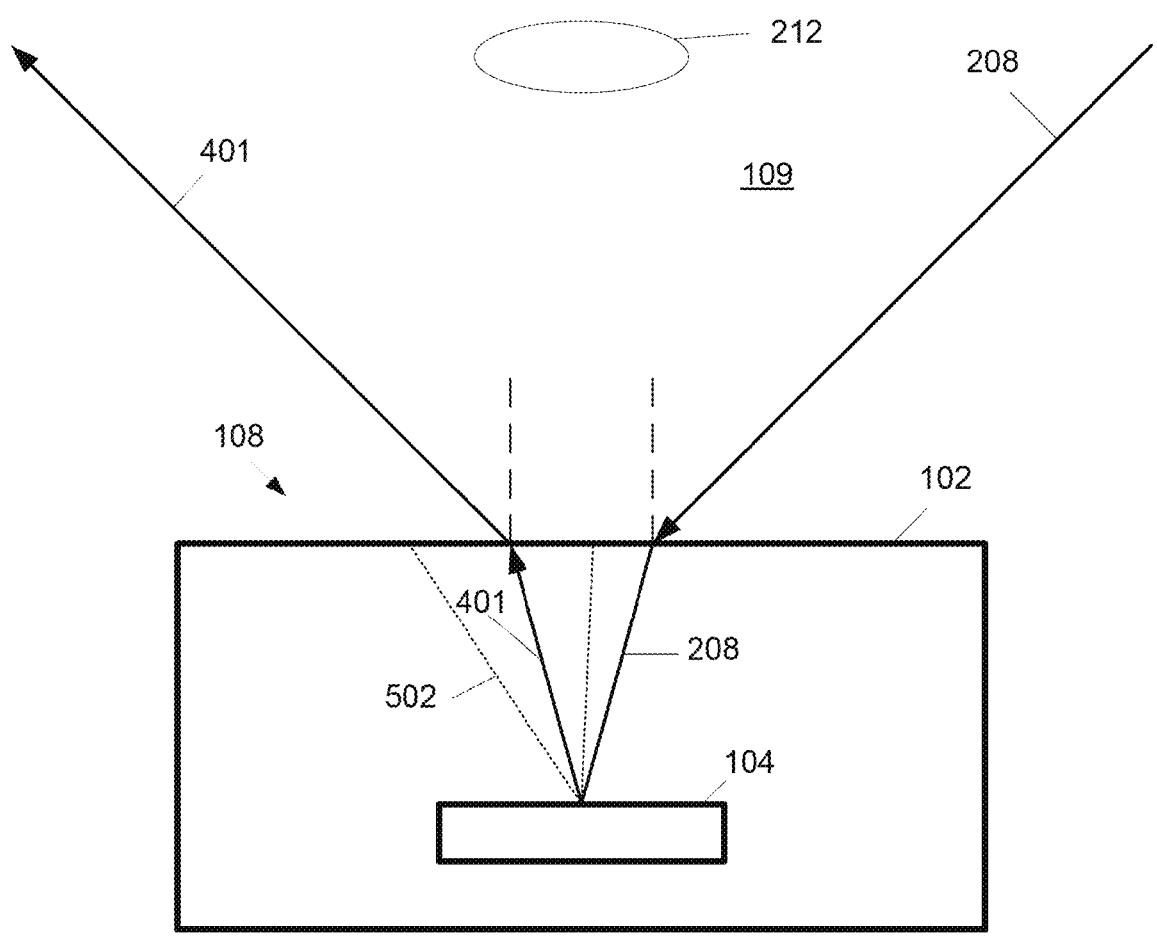
FIG. 5 illustrates one embodiment of the object of FIG. 1 showing a beam reflected off of the surface of a feature of the object over a range of angles.

FIG. 4 illustrates one embodiment of the object 102 illuminated by the beam 208 oriented at the angle 304 relative to normal of the surface of the object 102 (represented by normal dashed lines 402, 403). At the interface between the object 102 and the surrounding medium 109, the beam 208 may be refracted such that its angle relative to the normal 402 is shown by 404. When the surrounding medium 109 is air (index of refraction~1), the object 102 is a silicon substrate (index of refraction~3.5) and the angle 304 is about 45°, given Snell's law, the angle 404 may be about 11.6°. After entering the object 102, the incident beam 208 may reflect off of the feature 104, resulting in a reflected beam 401. The reflected beam 401 may be incident on the surface 108 between the object 102 and the surrounding medium 109 at the angle 404 relative to the normal 403. At the surface 108, the reflected beam 401 may be refracted to the angle 304 relative to the normal 403.

It can be seen that, as illustrated in FIG. 4, the reflected beam 401 is not incident on the objective 212 within its acceptance angle 306. At least two factors, however, allow portions of the beam 401 to be incident on the objective 212. First, as illustrated in FIG. 3, roughness on the surface 108 of the object 102 may cause the incident beam 208 to actually be incident on the feature 104 over a range of angles, represented by cone 312 shown in FIG. 3. Further, surface roughness of the feature 104 may cause the reflected beam 401 to be scattered over a range 502 of angles, including angles that allow a portion of the reflected beam 401 to be incident on the objective 212 within its acceptance angle (see FIG. 5). It will be appreciated that portions of the beam 401 follow paths similar to those shown in FIG. 4 and, therefore, such portions are not incident on the objective 212. Because a portion of the reflected beam 401 is lost, it may be desirable to choose an illumination source 202 having an intensity relatively greater than what would be used for a similar bright field imaging set-up. For example, in various embodiments, the intensity of the illumination source 202 may be an order of magnitude larger than that used for a similar bright field imaging set-up.

Figure 6:
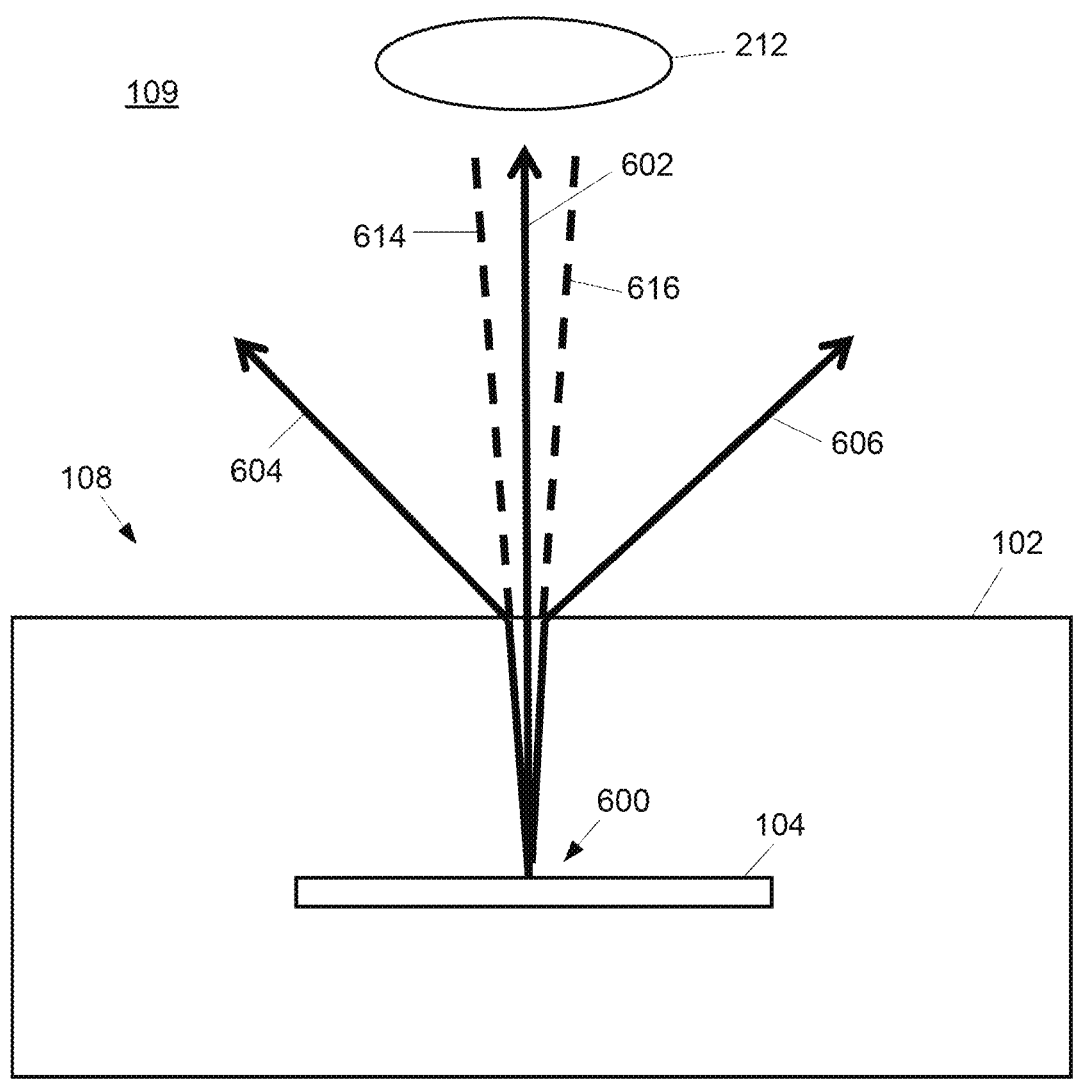
FIG. 6 illustrates one embodiment of the object and feature shown in FIG. 1 showing rays reflected by a point on the feature.

According to various embodiments, refraction at the interface between the surface 108 and the surrounding medium 109 may serve as a spatial filter, increasing the resolution of the image captured by the objective 212 by minimizing the spatial distribution of beams captured from each point of the feature 104. This effect, which can be thought of as an inverse of the Snell's window effect observed under water, is illustrated in FIG. 6. FIG. 6 shows one embodiment of the object 102 and feature 104 including rays 602, 604, 606 reflected by a point 600 on the feature 104. The ray 602 is incident on the surface/surrounding medium 109 interface at an angle within the acceptance range of the objective 212. Accordingly, the ray 602 is received by the objective 212 and transmitted to the imaging device 214 (see FIG. 2). The rays 604 and 606, in contrast, are outside of the acceptance range. As shown by un-refracted paths 614, 616, the rays 604, 606 would ordinarily be incident on objective 212 within its acceptance angle. Because of refraction, however, the rays 604, 606 are bent outside of the acceptance angle of the objective 212. As a result, the minimum spacing between subsurface objects 104 and 106 that can be resolved is based on the wavelength of the incident light 208 divided by the index of refraction of the substrate material 102, thus improving image resolution.

Figure 7:
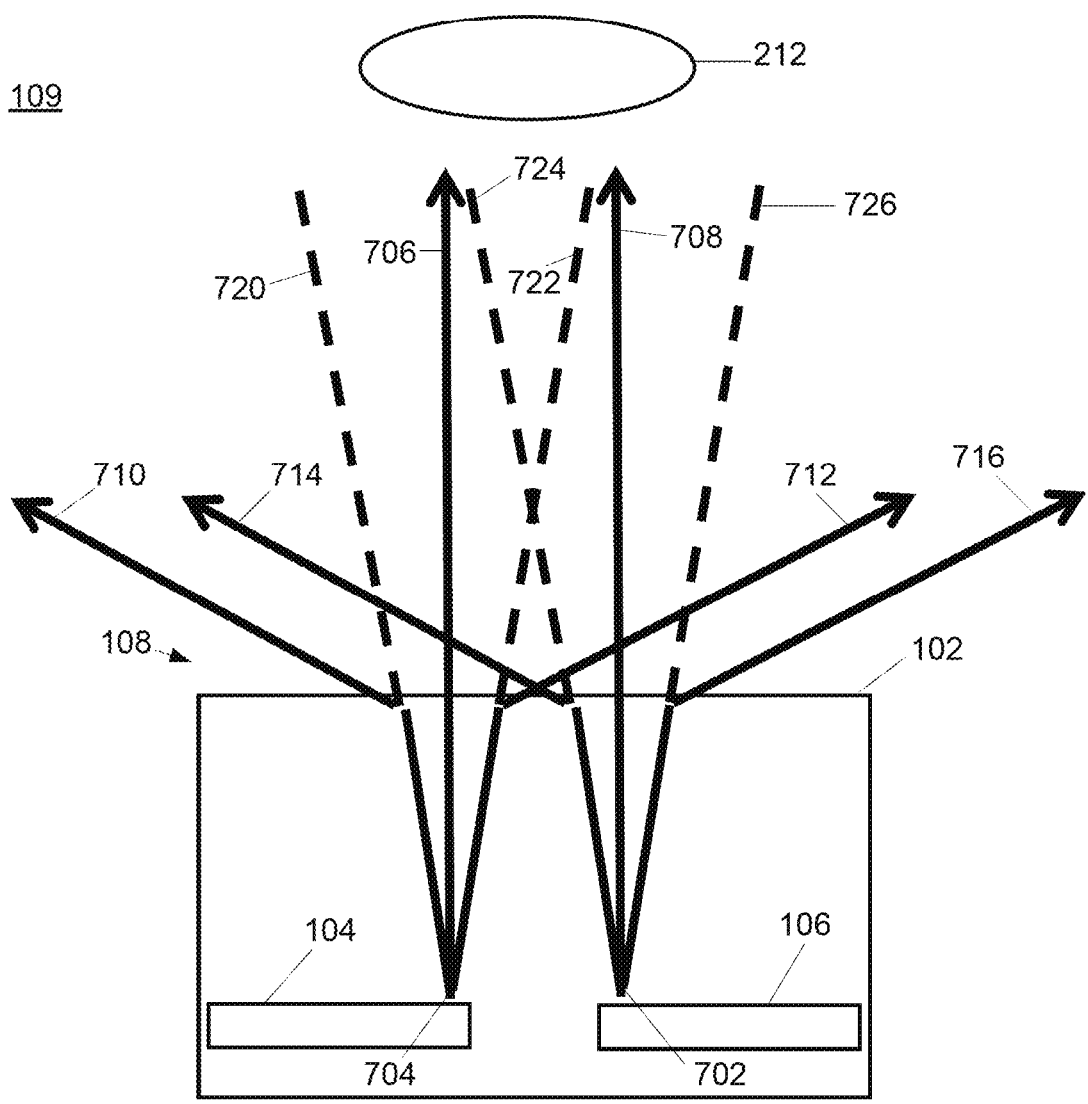

The utility of the spatial filtering effect is demonstrated by FIG. 7, which shows one embodiment of the object 102 showing both of the subsurface features 104, 106. Rays 706, 710 and 712 are reflected off of a point 704 on feature 104. Rays 708, 714 and 716 are reflected off of a point 702 on feature 106. As illustrated, rays 706 and 708 are within the acceptance range and, therefore, are incident on the objective 212. Rays 710, 714, 712 and 716, after refraction at the interface between the object 102 and the surrounding medium 109, are outside of the acceptance range and, therefore, are not incident on the objective 212. Dashed lines 720, 724, 722, 726 indicate the paths of the respective rays 710, 714, 712, 716 absent refraction at the object 102/surrounding medium 109 interface. It will be appreciated that, but for the refraction, ray 714 from point 702 would overlap ray 706 from point 704. This would result in fuzziness and lack of clarity in the resulting image (e.g., in the image, the border between feature 104 and feature 106 would be blurred). As shown, however, the refraction between the object 102 and the surrounding medium 109 minimizes beam overlap from nearby points, thus improving image quality.

Figure 8:
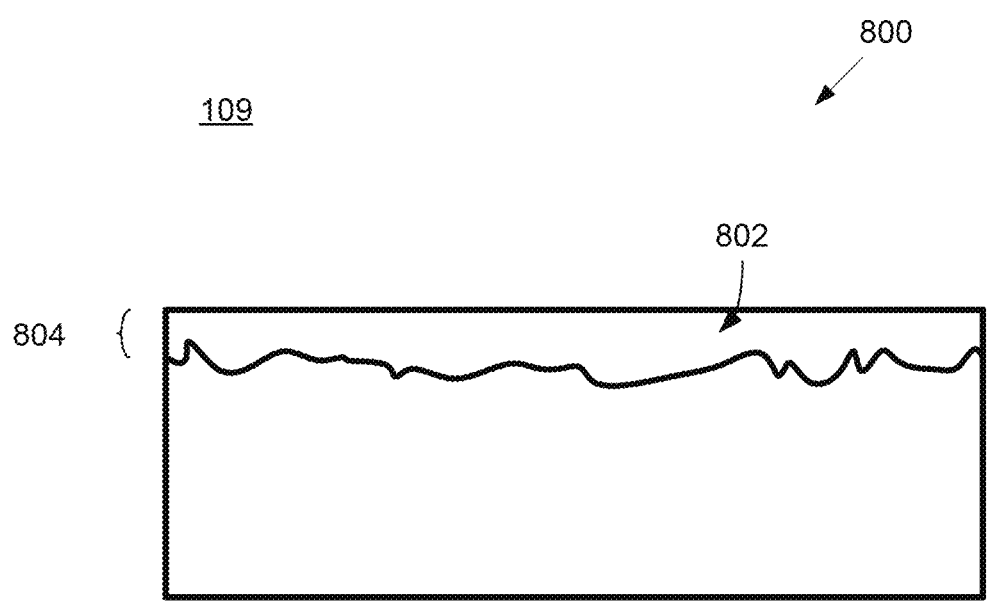
FIG. 8 illustrates a cross-sectional view of one embodiment of another object having surface features that may be observed utilizing the side addressed illumination techniques described herein.

Also, for example, the apparatuses and methods described herein may be used to image features on the surface of an object by providing a temporary or permanent layer of high refractive index material over the surface prior to imaging. For example, FIG. 8 illustrates a cross-sectional view of one embodiment of another object 800 having surface features 802. The surface features 802 may be imaged by providing a layer 804 of material having a high refractive index at the imaging wavelength range. The layer 804 may be deposited onto the object 800 using any suitable deposition technique. According to various embodiments, the layer 804 may be a fluid, such as an optical coupling fluid, that may be applied to the object 800 in any suitable manner. The layer 804 may be permanent or removable.

Figure 9:
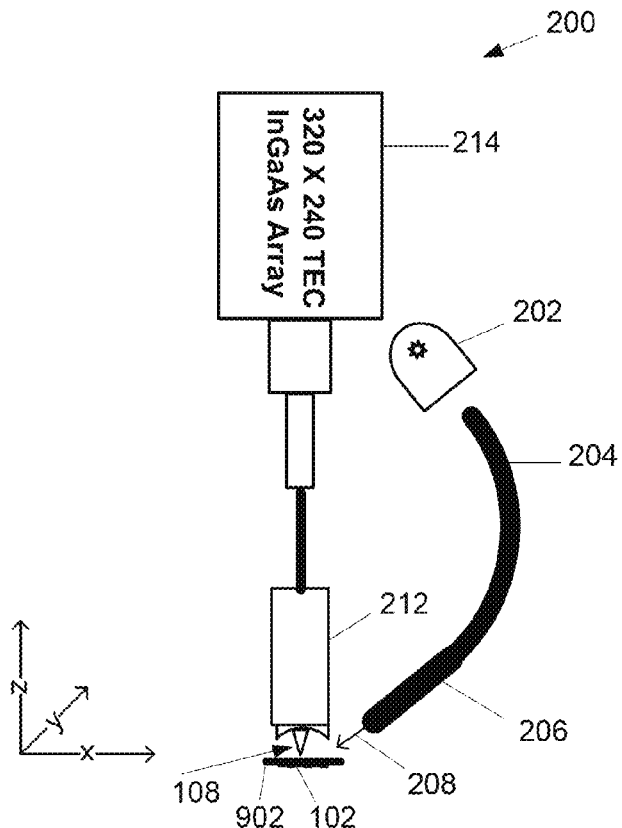
FIG. 9 shows one embodiment of the system of FIG. 2 including the imaging device, the object, the illumination source, and illumination directing elements such as, for example, the fiber optic bundle and collimating lens of FIG. 2.
Figure 10:
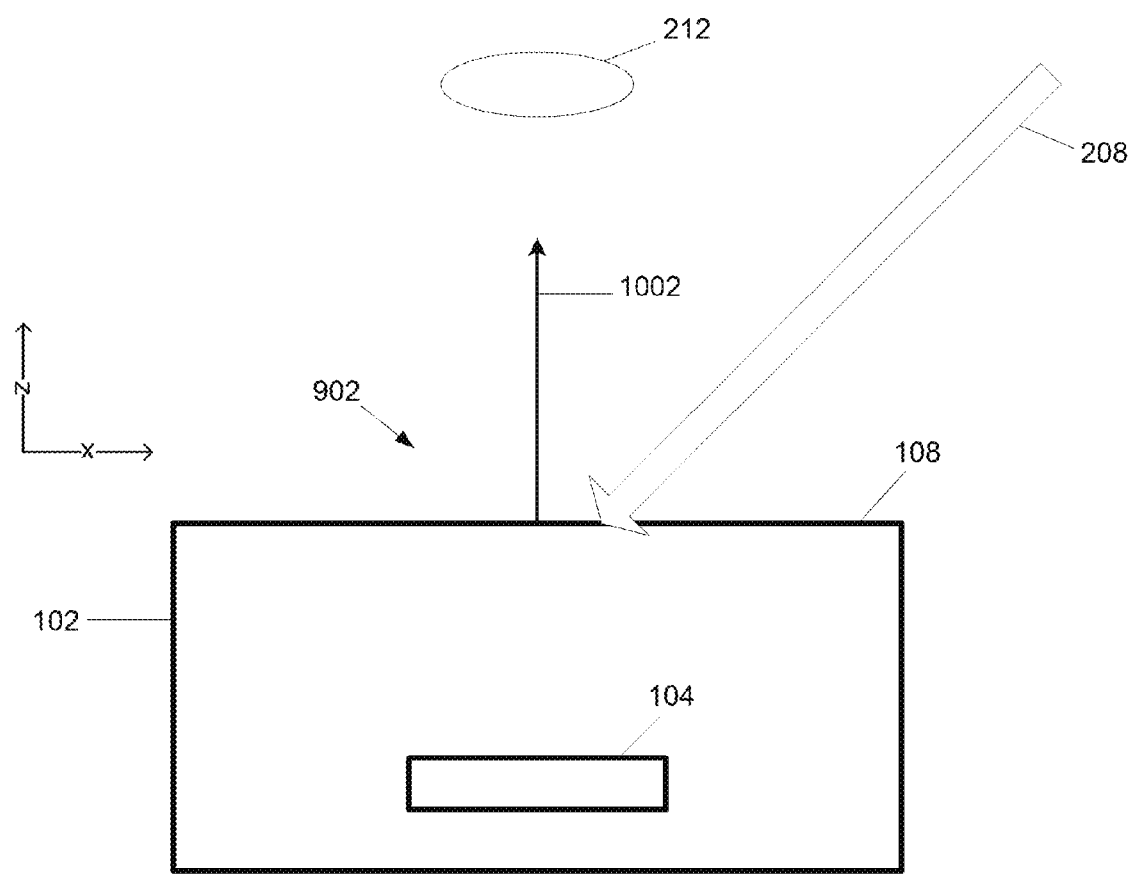
FIG. 10 illustrates a closer view of the object as illustrated in FIG. 9.

FIGS. 9 and 10 illustrate one embodiment of the system 200 configured to provide illumination from multiple directions (e.g., positions and angles). For example, FIG. 9 shows one embodiment of the system 200 including the imaging device 214, the illumination source 202, and illumination directing elements such as, for example, the fiber optic bundle 204 and collimating lens 206. Illumination beam 208 is shown incident on an imaging location 902 of the surface 108 of the object 102. Directions in FIG. 9 are indicated by the x, y and z axes shown. For example, the surface 108 may be in the x-y plane. The z-direction may be normal to the surface 108. FIG. 10 illustrates a closer view of the object 102 as illustrated in FIG. 9. A surface normal 1002 is illustrated normal to the surface 108 in the direction of the z-axis. For example, the surface normal 1002 may be directed from the surface 108 to the objective 212, as shown.

Figure 11:
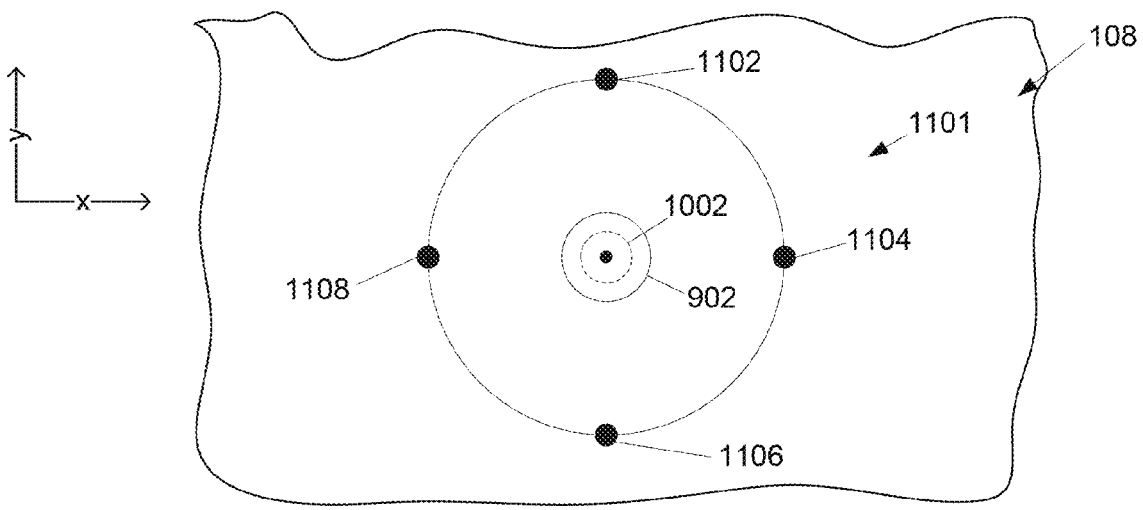
FIG. 11 illustrates a top view of the surface of the object of FIG. 10 showing an illumination array comprising four different illumination beams.

FIG. 11 illustrates a top view of the surface 108 showing an illumination pattern 1101 comprising illumination beams 1102, 1104, 1106, 1108. Each of the illumination beams 1102, 1104, 1106, 1108 may be incident on the imaging location 902 at an angle relative to the normal 1002. In some embodiments, all of the illumination beams 1102, 1104, 1106, 1108 are incident on the imaging location 902 at the same angle relative to the normal 1002. In other embodiments, different illumination sources 1102, 1104, 1106, 1108 are incident on the imaging location 902 at different angles relative to the normal 1002. As illustrated, each of the illumination beams 1102, 1104, 1106, 1108 is rotated about the normal 1002 in the x-y plane at various angles relative to one another. For example, the illumination beams 1104 and 1108 are shown rotated from the beam 1102 by +90° and −90°, respectively. The beam 1106 is shown similarly rotated from the source 1102 by 180°.

The various illumination beams 1102, 1104, 1106, 1108 may be generated by multiple, distinct illumination sources. In some embodiments, however, the beams 1102, 1104, 1106, 1108 are generated by a single illumination source that may be rotated or otherwise directed to the position of each beam 1102, 1104, 1106, 1108 shown in FIG. 11. Although four illumination beams 1102, 1104, 1106, 1108 are shown, it will be appreciated that additional beams may be omitted or added. For example, in some embodiments, it may be desirable to have three beams. A first beam may be considered to be positioned at 0°. A second beam may be rotated about the normal 1002 by +45°, and a third beam may be rotated about the normal 1002 by −45°. Also, FIGS. 13-15, described herein below, describe an example embodiment comprising twelve distinct illumination sources capable of generating twelve distinct illumination beams.

In some embodiments of the configuration illustrated in FIG. 11, all of the beams 1102, 1104, 1106, 1108 are illuminated at the same time. In this case, a single image of the imaging location 902 may be captured with all of the illumination beams 1102, 1104, 1106, 1108 active. In some embodiments, however, less than all of the beams 1102, 1104, 1106, 1108 are illuminated at the same time. For example, in some embodiments, the beams 1102, 1104, 1106, 1108 may be illuminated separately or in a combination of less than all of the beams 1102, 1104, 1106, 1108 (e.g., illumination pattern). An optimal illumination pattern may be determined, for example, as described herein. Also, in some embodiments, a separate image may be captured with each of a plurality of illumination patterns. The resulting images may be utilized in the process of determining an optimal illumination pattern. In some embodiments, some or all of the resulting images are composted or otherwise combined to form a composite image.

According to various embodiments, the illumination pattern for a particular object 102 may be selected based on the orientation of the surface 108 and any sub-surface features 104. For example, illuminating a surface 108 in a direction parallel to and in a direction perpendicular to sub-surface features 104, in some embodiments, provides increased resolution. When the object 102 is a semiconductor chip, the sub-surface features 104 may be arranged in a grid-like Manhattan-style configuration. Accordingly, at least two illumination beams may be directed at the imaging location 902, with the beams aligned with the grid of the sub-surface features 104 and separated from one another about the normal 1002 by 45°. When X-architecture chips or other non-Manhattan-style objects are imaged, different illumination beam directions may be selected to illuminate the parallel and perpendicular directions of major sub-surface features 104.

Figure 12:
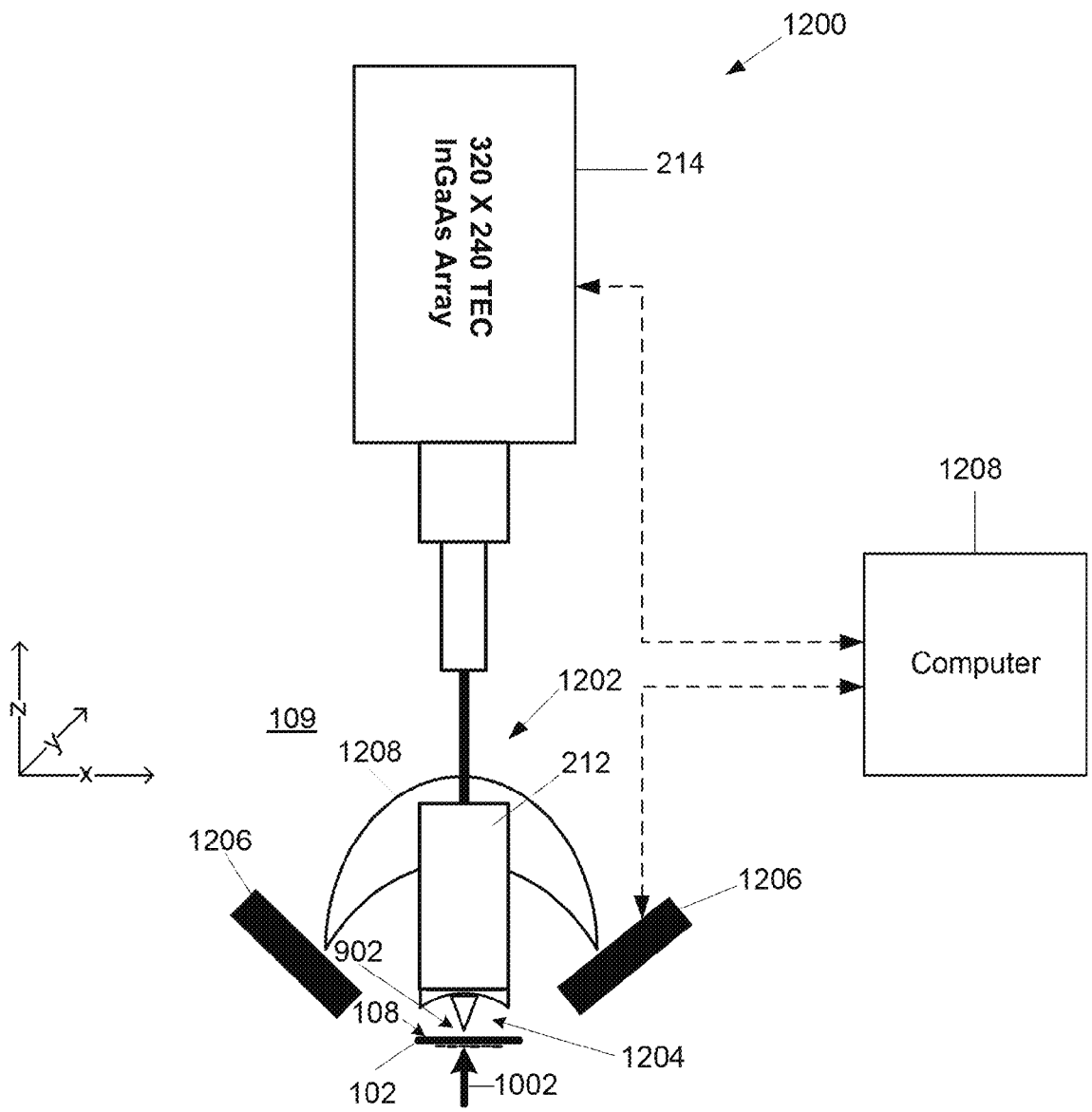
FIG. 12 illustrates one embodiment of a system comprising an illumination array that includes multiple illumination sources and a computer for optimizing an illumination pattern of the illumination array.

In some embodiments, however, the pattern of sub-surface or other features in or on an object may be too complicated to be optimally illuminated by the simple parallel and perpendicular illumination pattern described above. For example, some sub-surface features may be rounded rather than flat, some sub-surface features may be non-parallel, etc. Accordingly, an illumination array may comprise a plurality of illumination sources that may be utilized in conjunction with a computer or other processing device to determine an optimal illumination pattern. FIG. 12 illustrates one embodiment of a system 1200 comprising an illumination array 1202 that includes multiple illumination sources 1206 and a computer 1208 for optimizing an illumination pattern of the illumination array 1202. As illustrated, the system 1200 comprises an objective 212 and imaging device 214, for example, as described above. The illumination array 1202 is positioned to provide illumination for images of the object 102 captured by the imaging device 214. The individual illumination sources 1206 may be secured to a bracket 1208 or any other suitable frame or frames for fixedly securing the sources 1206. In some embodiments, the sources 1206 are movable. For example, the sources 1206 may rotate about the normal 1002 and/or may change angles relative to the normal 1002. In some embodiments, the sources 1206 are movable via servo motors and/or any other type of motion device (not shown), which may be under the control of the computer 1208. In some embodiments, the object 102, surrounding medium 109 and the angle of one or more of the sources 1206 relative to the normal 1002 are configured as described above to achieve the advantages of side-addressed illumination.

The computer 1208 may be programmed to implement an illumination pattern optimization algorithm, as described herein. For example, the computer 1208 may be in electronic communication with the imaging device 214 via any suitable communication bus utilizing any suitable protocol (e.g., universal serial bus (USB), etc.). The computer 1208 may be capable of instructing the imaging device 214 to capture an image of the imaging location 902 (as shown in FIG. 9). The computer 1208 may also be capable of receiving images captured by the imaging device 214. The captured images may be received in any suitable image file format including, Widows bitmap or BMP file format, Joint Photographic Experts Group (JPEG) format, Tagged Image File Format (TIFF) format, Graphics Interchange Format (GIF), etc. The computer 1208 may also be in electronic communication with the illumination array 1202. For example, the computer 1208 may be capable of instructing the array 1202, and the various sources 1206 thereof, to illuminate according to various different illumination patterns.

Figure 13:
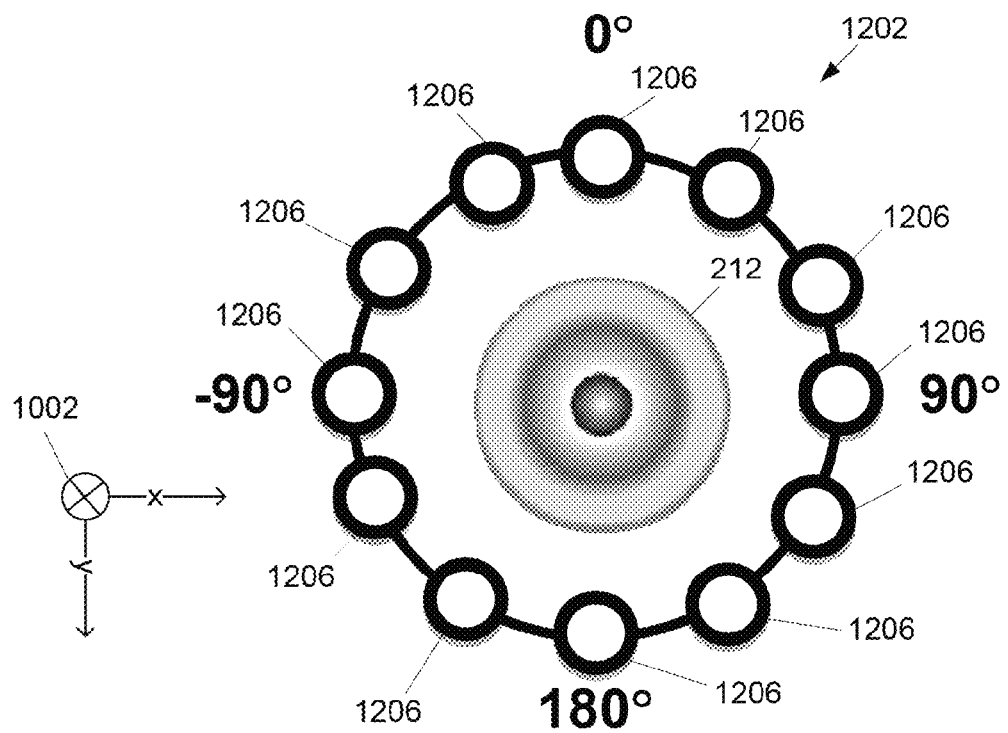
FIG. 13 illustrates a bottom-up view of one embodiment of the objective and illumination array showing one example configuration of the illumination sources.
Figure 14:
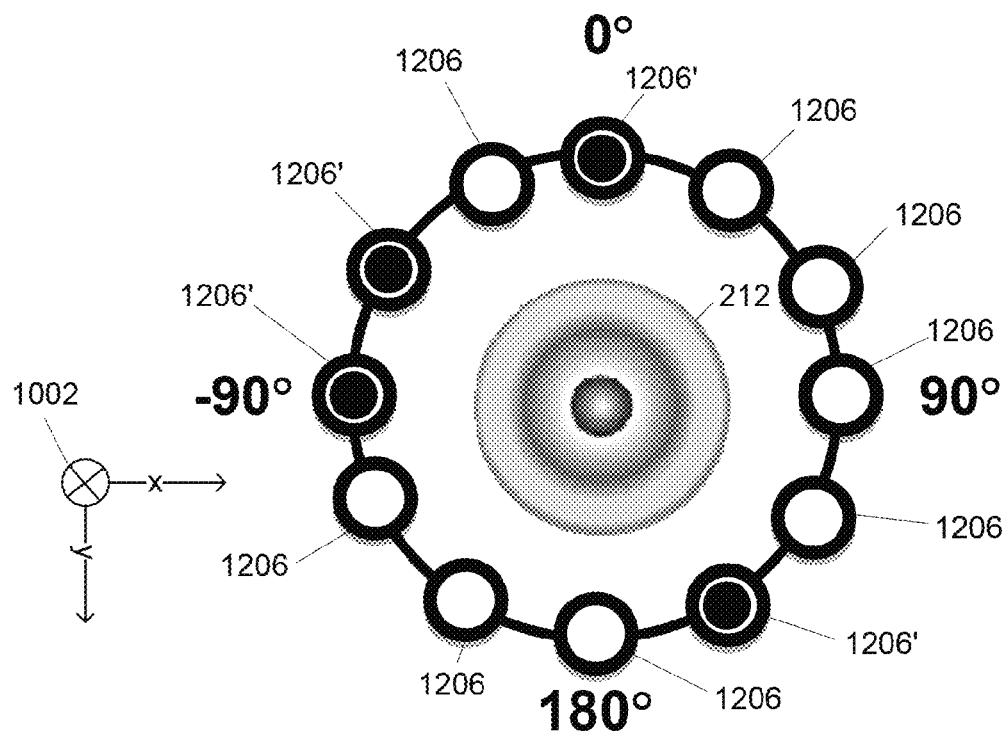
FIGS. 14-15 illustrates example embodiments of the objective and illumination array of FIG. 13 showing example illumination patterns in which illumination sources are activated.
Figure 15:
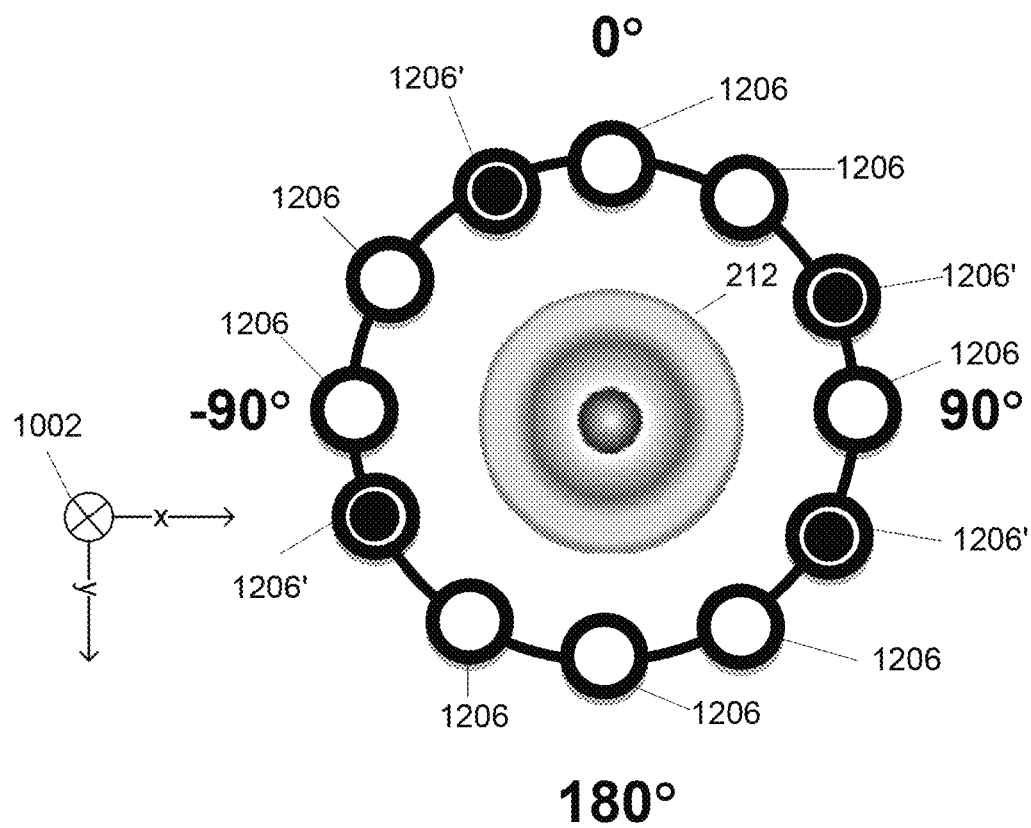
Figure 16:
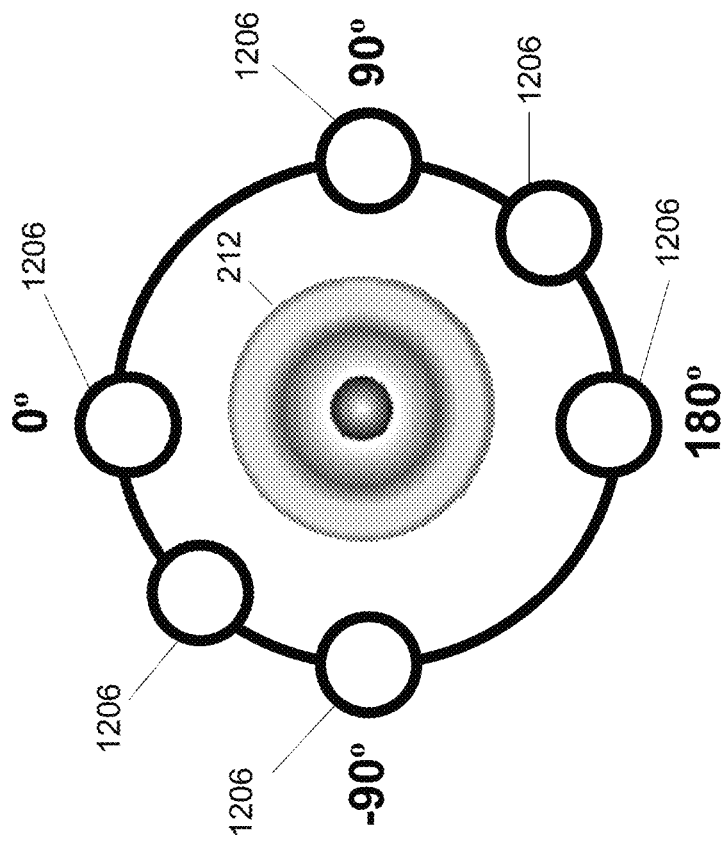
FIG. 16 illustrates a bottom-up view of one embodiment of the objective and illumination array of FIG. 12 illustrating an asymmetrical configuration of illumination sources.
Figure 16:
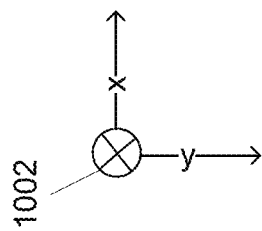

FIG. 13 illustrates a bottom-up view of one embodiment of the objective 212 and illumination array 1202 showing one example configuration of the illumination sources 1206. In FIG. 13, twelve, (12) illumination sources 1206 are positioned at different angles in the x-y plane relative to the objective 212 around the normal 1002. (The normal 1002 is illustrated in FIG. 13 in conjunction with the x-y axis marker so as to avoid obscuring the objective 212.) It will be appreciated that different objects 102 may be optimally illuminated by different combinations of the illumination sources 1206. FIG. 14-15 illustrate example embodiments of the objective 212 and illumination array 1202 of FIG. 13 showing example illumination patterns in which illumination sources 1206' are activated. The activated sources 1206' may provide illumination at a common intensity and/or at different intensities. It will be appreciated that the illumination sources 1206 of the illumination array may be arranged in any suitable configuration. For example, FIG. 16 illustrates a bottom-up view of one embodiment of the objective 212 and illumination array 1202 of FIG. 12 illustrating an asymmetrical configuration of illumination sources 1206. The illumination sources 1206 as illustrated in FIG. 16 are not symmetrical about the x and y axis, though any suitable asymmetry may be used.

Figure 17:
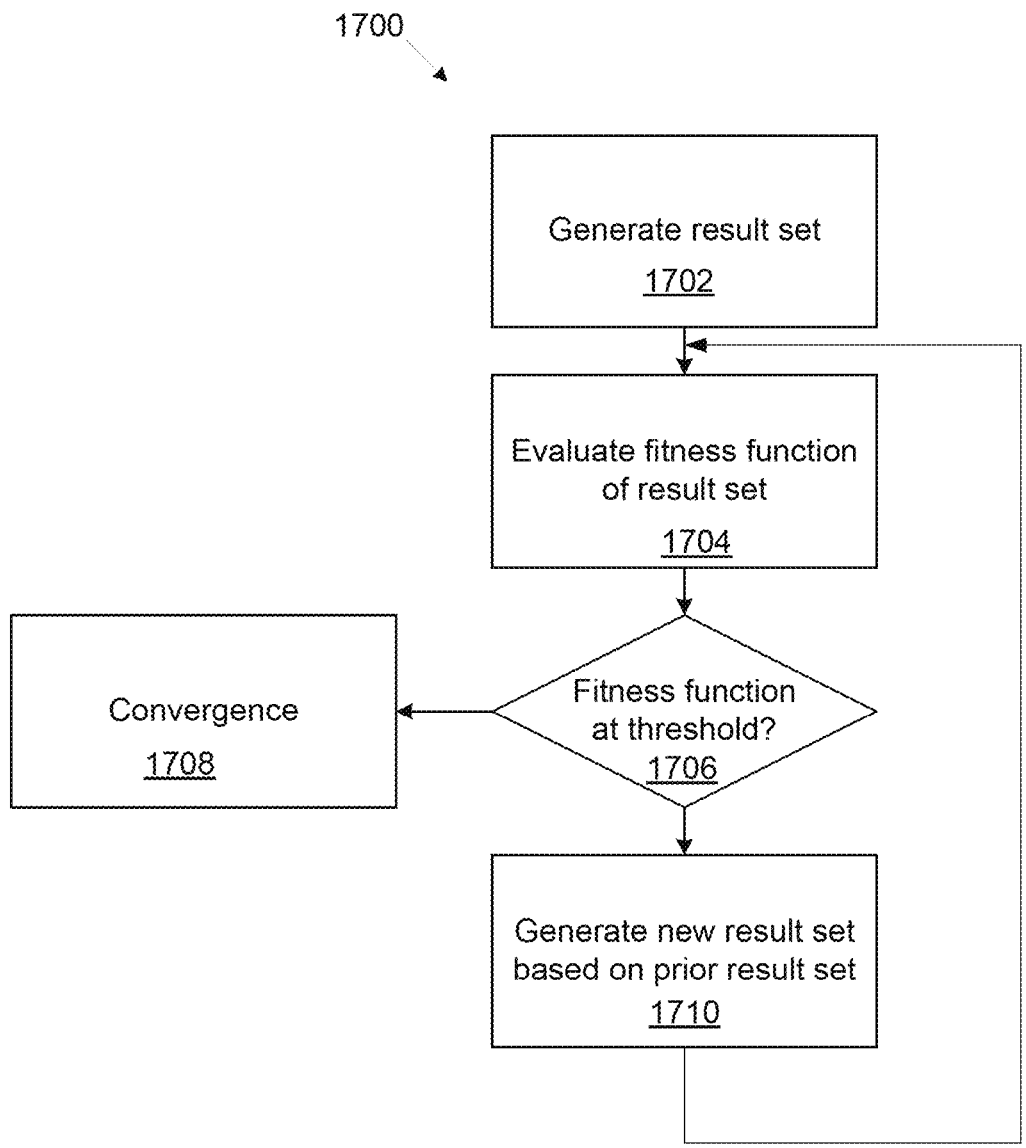
FIG. 17 illustrates a flow chart showing one embodiment of a process flow that may be executed by the computer of FIG. 12 to select one or more optimal illumination patterns.

Referring back to FIG. 12, the computer 1208 may be utilized to derive one or more optimal illumination patterns that may be delivered by the illumination array 1202 for imaging of the object 102. Any suitable optimization algorithm may be used. FIG. 17 illustrates a flow chart showing one embodiment of a process flow 1700 that may be executed by the computer 1208 to select one or more optimal illumination patterns. The process flow 1700 demonstrates the implementation of a global search algorithm, such as an evolutionary algorithm or a particle swarm optimizer algorithm, sometimes referred to as a swarm algorithm. At 1702, the computer 1208 may generate and/or receive a first result set. The result set may comprise one or more illumination patterns (e.g., patterns capable of being generated by the illumination array 1202). The illumination patterns included in the first result set may be selected in any suitable manner. For example in some embodiments, the illumination patterns for the first result set are randomly selected. In some embodiments, the illumination patterns for the first result set are selected by a human operator based on "dead reckoning" or a best guess of what the optimal illumination pattern will be.

At 1704, the computer 1208 may evaluate a fitness function for each of the illumination patterns included in the first result set. For each illumination pattern, the computer 1208 may instruct the illumination array 1202 to illuminate according to the illumination pattern. With the illumination pattern implemented by the illumination array 1202, the computer 1208 may instruct the imaging device 214 to capture an image of the object 102. The resulting image may be evaluated in any suitable manner to determine a fitness function value of the illumination pattern. The fitness function value may be calculated for the entire image and/or for a region of interest (ROI) of the image that may be selected by an operator of the system. In some embodiments, described in more detail below, the fitness function is evaluated considering an intensity contrast of the image.

Upon finding a fitness function for each of the illumination patterns of the first result set, the computer 1208 may determine, at 1706, if any of the fitness functions are at a defined threshold. The threshold may define a point where an illumination pattern associated with a fitness function is either the optimal illumination pattern (e.g., the algorithm has converged) and/or is within a desired tolerance of the optimal illumination pattern. If the fitness function of at least one of the illumination patterns is at or above the threshold, then the algorithm may be considered to have converged at 1708. The illumination pattern or patterns having fitness functions greater than or equal to the threshold may be considered an optimal illumination pattern or pattern for the combination of the system 1200 and object 102 and may be used for subsequent images of the object 102 using the system 1200. If none of the calculated fitness functions reach the threshold, the computer 1208 may, at 1710, generate a new result set based on the first result set (and/or the calculated fitness function values). The new result set may represent an additional iteration or generation of the algorithm. At 1704, the computer may calculate fitness function values for the new result set. In some embodiments, the process continues until the computer 1208 identifies an optimal illumination pattern (e.g., converges) and/or is within a desired tolerance of the optimal illumination pattern.

The fitness function calculated above at 1704 may be any suitable function yielding a value or values that indicate the quality of the measured illumination pattern as expressed, for example, by the quality of the resulting image. In various embodiments, the fitness function yields a single number value that acts as a quantitative measure of the quality of the measured illumination pattern. Any fitness function capable of yielding fitness function values that discern differences between different lighting conditions may be used. For example different acceptable fitness functions may measure different aspects of image quality. One type of fitness function may measure the intensity contrast of an image. Other types of fitness functions may utilize edge enhancement algorithms, matching filters, recognition algorithms, etc.

Equation (1) below provides an example fitness function based on the modulation contrast of a structure that has alternating light and dark areas:

$$C = \frac{I_{min} - I_{max}}{I_{min} + I_{max}} \quad (1)$$

In Equation (1), C is contrast and $I_{min}$ and $I_{max}$ are minimum and maximum intensities of the object 102 (e.g., the minimum and maximum pixel values indicated in the image of the object 102). In some embodiments, the process flow 1700 is executed to optimize the contrast C in order to maximize the imaging contrast of the subsurface features 104 of the object 102.

When the illumination optimization systems and methods described herein are implemented in the context of a microscope system, it will be appreciated that some sub-surface features 104 may be small enough to exceed a maximum resolution of the imaging system. In such cases, a modulation transfer function (MTF) of the optical system may be quantified. The MTF is a measure of the maximum contrast (C) that can be measured by an optical system for a given spatial periodicity of alternating light and dark structures (e.g., the subsurface features 104 of the object 102, substrate, etc.). For semiconductor applications, the distance between alternating light and dark regions is typically measured in lines per millimeter (lines/mm). As the spacing between dark and light elements becomes smaller, the C between the elements decreases until the optical system can resolve only a grey line. The MTF for the optical system may indicate the minimum observable distance between light and dark structures before the optical system returns such a grey line.

In some embodiments utilizing a modulation contrast as a fitness function, the fitness function threshold is reached when, the maximum achievable C according to the measured MTF of the optical system is reached, the measured C does not change after a predetermined number of algorithm generations and/or when the measured C has met a predetermined value (e.g., a user predetermined value). In some embodiments, the optical system (e.g., imaging device 214 and objective 212) may have its MTF measured before optimization. Values for the MTF may be stored, for example, at the computer 1208 as a look-up file or in any other suitable data structure.

In one example use case, the object 102 may comprise a structure on a microelectronic device having two metal lines separated by 1 µm with semiconductor material between them. Under illumination, as described herein, the metal lines reflect illumination and are "light," while the semiconductor passes or absorbs the illumination and are "dark." An operator of the system 1200 may select the metal lines as a region-of-interest (ROI) in the resulting image. FIG. 18a illustrates an image 800 that may be imaged by the system of FIG. 12. The image 800 shows an ROI 802 that may be selected by the operator. The ROI 802, illustrated in more detail in FIG. 18b, includes metal lines separated by 1 µm, as described above. In various embodiments, the ROI 802 may be selected at any suitable size. For example, it may be a portion of the image, as shown, or the entire image. The computer 1208 may take a modulation contrast-related fitness function value (e.g., C) of the ROI 802. For example, the computer 1208 may be configured to take one dimensional lineouts (e.g., entire rows or columns from the ROI 802 that will result in one dimensional arrays). The lineouts may be taken horizontally and/or vertically. For each lineout, C may be calculated considering the alternating light and dark regions. FIG. 19a illustrates the ROI 802 of FIG. 18a indicating an example horizontal lineout 804. FIG. 19b illustrates an intensity plot of the horizontal lineout 804 of FIG. 19a.

Figure 18:
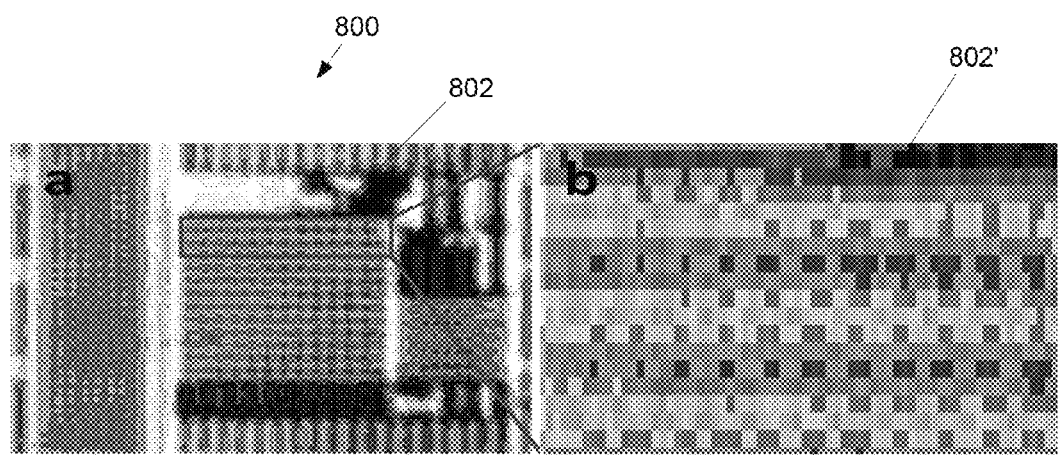
Figure 19:
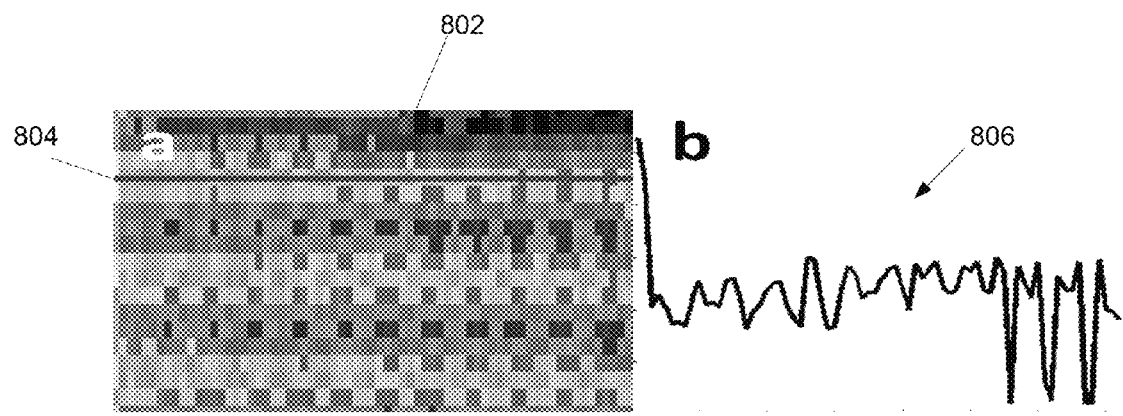
Figure 20:
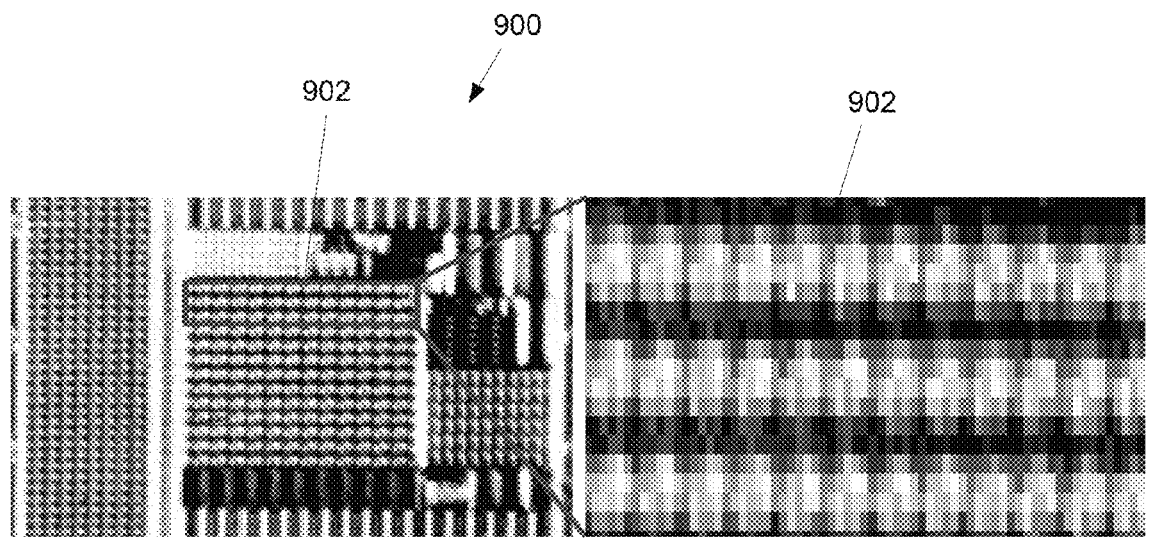
FIG. 20 illustrates an image that may be imaged by the system of FIG. 12 taken under an optimized illumination pattern determined according to the process flow of FIG. 17.

In various embodiments, an average C may be taken over the ROI 802. In some embodiments, average C's are calculated for both the horizontal and vertical lineouts. Separate horizontal and vertical C's may be considered separately and/or averaged to find a single C (in this example, the fitness function value) for the ROI 802. The process may be repeated to find fitness function values for images taken under different illumination patterns, as described with respect to FIG. 17. In some embodiments, a maximum limit on image intensity (e.g., the intensity of each pixel) may be set so as to avoid saturating the imaging device 214. FIG. 20 illustrates an image 900 that may be imaged by the system of FIG. 12 taken under an optimized illumination pattern determined according to the process flow 1700 of FIG. 17. The image 900 depicts the same semiconductor and metal lines as shown in FIGS. 18-19.

Figure 21:
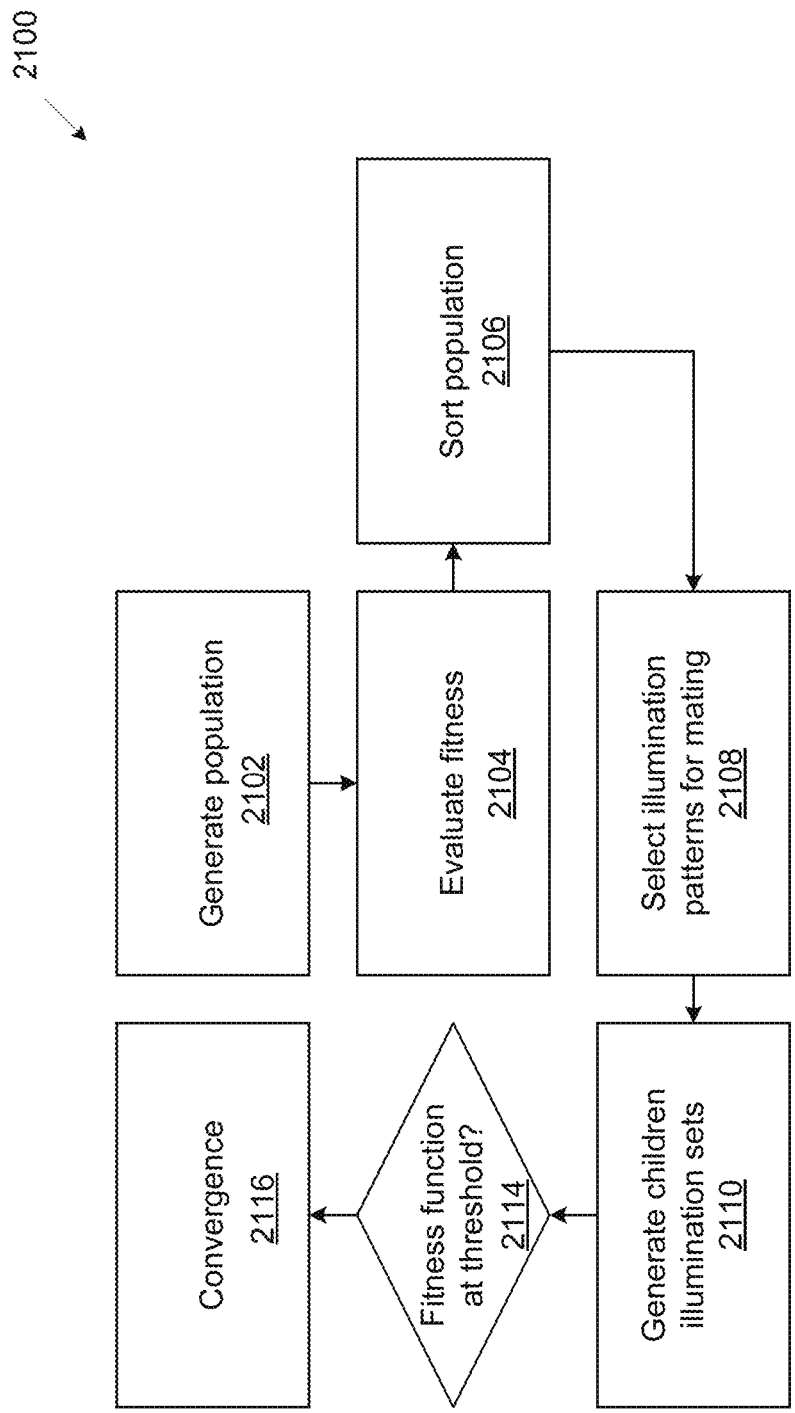
FIG. 21 illustrates a flow chart showing one embodiment of a process flow that may be executed by the computer of FIG. 12 to select one or more optimal illumination patterns according to an evolutionary algorithm.

As described above, any type of optimization algorithm may be utilized by the computer 1208 to determine an optimal illumination pattern or patterns for the illumination array 1202 to illuminate a particular object 102. FIG. 17, described above, illustrates a generic implementation of a global search algorithm. It will be further appreciated that the computer 1208 may implement any suitable global search algorithm. For example, in some embodiments, the computer 1208 selects an optimal illumination pattern or patterns according to an evolutionary algorithm, a particle swarm optimizer algorithm, or a hybrid algorithm. FIG. 21 illustrates a flow chart showing one embodiment of a process flow 2100 that may be executed by the computer 1208 of FIG. 12 to select one or more optimal illumination patterns according to an evolutionary algorithm. At 2102, an initial population of illumination patterns may be generated. The initial population, similar to the first result set at 1702 above, may be generated in any suitable manner. In some embodiments, the initial population is generated randomly (e.g., by the computer 1208). In some embodiments, the initial population is generated randomly with a given distribution size determined by a Gaussian distribution. In some embodiments, the initial population is generated around a solution (or what is believed to be close to the optimal illumination pattern). The initial population may be evaluated utilizing a fitness function at 2104. For example, 2104 may correspond to the action 1704 from the process flow 1700.

After application of the fitness function, the initial population may be sorted at 2106, for example, in order of fitness function value. At 2108, the computer 1208 may select a set of one or more illumination patterns for mating (e.g., a mating set). The selected illumination patterns may include patterns having high fitness function values. For example, in some embodiments, the top N percent of illumination patterns by fitness function values are selected, where N is any suitable value. At 2110, the computer 1208 may generate child illumination patterns from the mating set. For example, action 2110 may correspond to action 1710 of the process flow 1700 described herein above. At 2110, the child illumination patterns may be generated using any suitable operator or operators. In some embodiments, the number of illumination patterns in the mating set and the number of child illumination patterns selected by the operator or operators may be weighted or otherwise predetermined at the beginning of optimization so that the number of individual illumination patterns analyzed remains constant from one generation to the next.

Figure 22:
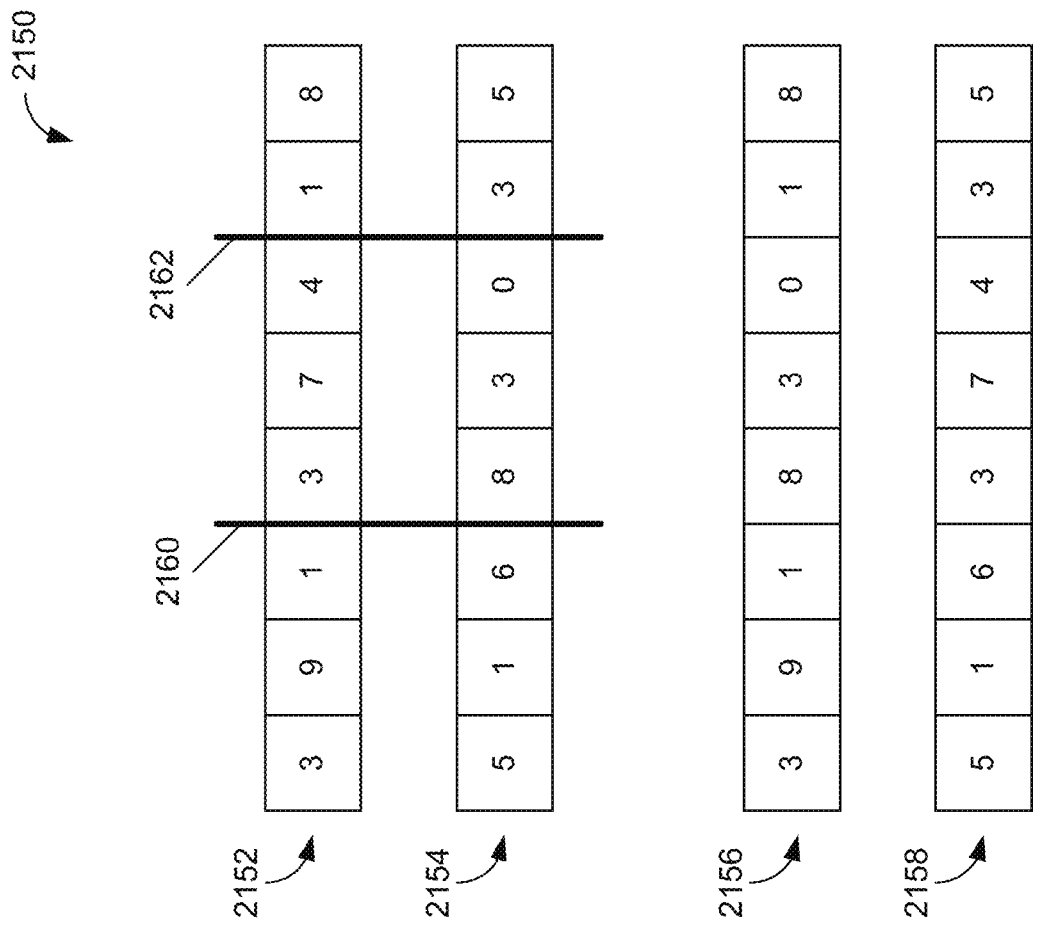
FIG. 22 is a block diagram of a set of parent illumination patterns and a set of child illumination patterns generated utilizing a two-point crossover operator.

In one example embodiment, three operators may be used including a mutation operator, a two-point crossover operator and an elitism operator. The mutation operator may randomly change a portion of an individual illumination pattern (e.g., the intensity of illumination provided by different sources 1206 of the illumination array 1202) with some small frequency. A two-point crossover operator may swap spliced portions of parent illumination patterns to generate child illumination patterns. FIG. 22 is a block diagram of a set of parent illumination patterns 2152, 2154 and a set of child illumination patterns 2156, 2158 generated utilizing a two-point crossover operator. Each of the illumination patterns 2152, 2154, 2156, 2158 may comprise a series of numbers where each number corresponds to an intensity of illumination provided by sources 1206 of the array 1202. Each of the parent patterns 2152, 2154 may be split at two positions 2160, 2162. Pattern values between the two positions may be swapped, generating the two new child illumination patterns 2156, 2158.

According to an elitism operator, a set of one or more best individual illumination patterns may pass unchanged from one generation to the next. The best individual illumination patterns may be the patterns from the mating set that have the highest fitness function values. The number of best individual illumination patterns may be selected in any suitable way and, in some embodiments, may be predetermined. In some embodiments, an elitism operator serves to prevent the algorithm from mutating away from the best values that it has already discovered (e.g., getting lost). The elitism operator may be most value in early generations of an optimization and, in some embodiments, is utilized only in the early generations of an optimization (e.g., for the first N generations).

Other example operators that may be used include an average crossover, one-point crossover, smooth creep, one point blend, islanding, etc. A smooth operator may make incremental changes to parent illumination patterns to smooth out discontinuous portions of the pattern. A creep operator may make incremental changes to parent illumination patterns to slightly change its values. An average crossover operator may average the values of two illumination patterns together to generate a single child pattern. A one point blend operator may be similar to an average crossover value, but for just a single value of an illumination pattern. An islanding operator may create multiple instances of subpopulations with periodic migrations of the strongest individual patterns between islands. Referring back to FIG. 21, it will be appreciated that generating child illumination patterns at 2110 may utilize any of the operators described herein, as well as other operators, in any suitable configuration or pattern. In various example embodiments, all individual illumination patterns are considered for reproduction via each operator. The probability that an illumination pattern will be chosen for reproduction may be determined either by random, or by using a fitness dependent weighting criteria that gives more fit illumination patterns a better chance at reproducing than less fit illumination patterns. At 2114, the computer 1208 may evaluate the fitness function values for the child illumination sets generated at 2110. If one or more of the child illumination sets converge at 2116, the algorithm may be complete. If not, an additional generation of the illumination sets may be generated (e.g., beginning at 2106).

In some example embodiments, as described herein above, a GSA algorithm may be and/or utilize aspects of a particle swarm optimization algorithm or swarm algorithm. Particle swarm optimization algorithms are modeled after the swarming characteristics of bees and other similar creatures. Initially, a set of "particles" are randomly distributed in a search space. Each particle may correspond to an illumination set from the first result set (See FIG. 17). Each particle may be provided with a random velocity, where the velocity indicates a direction and speed of changes made to the particle. As each particle moves a time step (e.g., one iteration of the algorithm), the fitness function for the illumination set is found. A best position for each particle (e.g., value of the particle when the best fitness function value is yielded) as well as a best global position (e.g., the illumination set corresponding to the best fitness function value) is stored. The velocity of each particle may be updated considering one or more of the following four parameters: a best individual position of the particle ($p_{id}$); a globally best position ($p_g$); a cognitive constant $\Phi_c$; and a social constant $\Phi_s$. In some embodiments, these parameters may be utilized to update the velocity of each particle according to Equation (2) below:

$$v_{i+1} = v_i + \Phi_c(p_{id} - x_i) + \Phi_s(p_g - x_i); \quad (2)$$

In Equation (2), $x_i$ is a current position of the particle. A new position after a time step is given by Equation (3) below:

$$x_{i+1} = x_i + v_{i+1} \quad (3)$$

Simple Newtonian expressions may be used to update the particle position and velocity until convergence is obtained.

Also, in some embodiments, a GSA algorithm may be and/or utilize a hybrid algorithm having aspects of a genetic algorithm and a particle swarm optimizer algorithm. Such hybrid algorithms may retain positive aspects of both genetic algorithms and particle swarm optimizer algorithms and may lead to efficiently determined optimal solutions regardless of problem structure. In one example embodiment, the computer 1208 may run a genetic algorithm for a threshold number of generations and/or until a fitness function value or values reaches a predetermined level, at which point a particle swarm optimization algorithm is used until convergence is reached.

According to an additional hybrid algorithm, a single initial set of illumination patterns is used for concurrent implementations of a genetic algorithm and a particle swarm optimizer algorithm. Following every fitness evaluation (e.g., generation), each algorithm may be allowed to contribute to a new generation of individual illumination patterns. The magnitude of each algorithms contribution may be determined based on the performance of the algorithm. For example, in some embodiments, a set of patterns from one generation having the highest fitness function value may be passed into the next generation of both algorithms regardless of the algorithm of origin.

According to another hybrid algorithm, two populations of illumination patterns are initially generated with both being equal in size. One population may be made up of genetic algorithm individuals while the other may contain particle swarm optimizer particles. Both algorithms may operate simultaneously and separately on the respective populations, allowing both algorithms to compete for a solution. In some embodiments, after a certain number of iterations, the particle swarm optimizer algorithm particle with the worst fitness value may be replaced by a copy of the genetic algorithm individual having the best fitness value. This may serve as a controlled method of exchanging information between the genetic algorithm and the particle swarm optimizer algorithm.

In some embodiments, the particular optimization algorithm used may be selected based on tests of multiple algorithms according to any suitable evaluation criteria. One such set of evaluation criteria is the De Jong test suite. The De Jong test suite comprises five functions that are commonly used to test the performance of optimization algorithms. Each of the functions is designed to simulate a particular problem and provide a straightforward method of evaluating an algorithm's ability to overcome certain difficulties in optimization. Optimization algorithms for illumination patterns, as described herein, may be evaluated using any of the De Jong test functions. In some embodiments, though, the Sphere function and Step function may be used. The Sphere function is given by Equation 4 below:

$$f1(x_i) = \sum_{i=0}^{n} x_i^2 \qquad (4)$$

The Step function is given by Equation (5) below:

$$f3(x_i) = \sum_{i=0}^{n} \lfloor x_i \rfloor \qquad (5)$$

In Equations (4) and (5), $x_i$ represents the genes or variables used in the algorithm to represent the properties of illumination patterns. The variable n in Equations (4) and (5) represents the number of genes or variables that are used for the optimization.

In some embodiments, the computer 1208 may be programmed to implement multiple optimization algorithms, for example, according to any of the descriptions herein. Upon implementation, each of the algorithms may be evaluated using any suitable evaluation method including, for example, the Sphere and Step functions of the De Jong test suit reproduced above. Optimization algorithms having the strongest evaluation may be maintained.

Various embodiments described herein may be modified to tilt the direction of the objective away from the surface normal. For example, a first image may be captured with the objective tilted off of the surface normal by a first angle. A second image may be captured with the objective tilted off of the surface normal by a second angle. The two images may be combined, forming a composite image. According to various embodiments, the direction of the objective at the first angle, the direction of the objective at the second angle, and at least one illumination beam may be coplanar.

Various embodiments described herein may be modified to discern areas of a semiconductor component having different doping properties (e.g., different bandgap energies). For example, the illumination source may be configured to generate illumination having a wavelength with an associated photonic energy that is substantially equal to the bandgap of a doped region of the semiconductor component. As a result, the doped region may attenuate the illumination causing the doped region to appear dark or shaded in the resulting image. Also, in some embodiments, the wavelength of the illumination source may be selected with a photonic energy substantially equal to the bandgap of an un-doped region of the semiconductor component, causing the un-doped region to appear dark or shaded. In various embodiments, the wavelength of the illumination source may be variable. For example, the illumination source may be set to various wavelengths corresponding to the bandgap energies of differently doped regions in the semiconductor component. Each of the differently doped or un-doped regions may appear as a dark or shaded region when the illumination corresponding to each region's bandgap is active.

According to various embodiments, some or all of the embodiments described herein may also be used in conjunction with a polarization techniques. For example, a polarizer may be placed in an optical path between the illumination source and the imaging device. The polarizer may be oriented with a polarization direction parallel to the illumination beam (e.g., perpendicular to the surface of the object). In this way, specular reflection off of the surface of the object may either be minimized (e.g., if the illumination beam is polarized) or its detection may be minimized (e.g., if the polarizer is placed in the path of the imaging device).

Although the figures above are described in the context of backside imaging of semiconductor devices, it will be appreciated that the apparatuses and methods disclosed herein may be used in various other contexts as well. For example, the apparatuses and methods used herein may be used to image any subsurface features where the index of refraction of material between a surface of an object and subsurface features of the object is relatively greater than that of the surrounding medium 109.

Various embodiments of computer-based systems and methods of the present invention are described herein. Numerous specific details are set forth to provide a thorough understanding of the overall structure, function, manufacture, and use of the embodiments as described in the specification and illustrated in the accompanying drawings. It will be understood by those skilled in the art, however, that the embodiments may be practiced without such specific details. In other instances, well-known operations, components, and elements have not been described in detail so as not to obscure the embodiments described in the specification. Those of ordinary skill in the art will understand that the embodiments described and illustrated herein are non-limiting examples, and thus it can be appreciated that the specific structural and functional details disclosed herein may be representative and illustrative. Variations and changes thereto may be made without departing from the scope of the claims.

Reference throughout the specification to "various embodiments," "some embodiments," "one embodiment," or "an embodiment," or the like, means that a particular feature, structure, or characteristic described in connection with the embodiment is included in at least one embodiment. Thus, appearances of the phrases "in various embodiments," "in some embodiments," "in one embodiment," or "in an embodiment," or the like, in places throughout the specification are not necessarily all referring to the same embodiment. Furthermore, the particular features, structures, or characteristics may be combined in any suitable manner in one or more embodiments. Thus, the particular features, structures, or characteristics illustrated or described in connection with one embodiment may be combined, in whole or in part, with the features structures, or characteristics of one or more other embodiments without limitation.

In general, it will be apparent to one of ordinary skill in the art that at least some of the embodiments described herein may be implemented in many different embodiments of software, firmware, and/or hardware. The software and firmware code may be executed by a processor or any other similar computing device. The software code or specialized control hardware that may be used to implement embodiments is not limiting. For example, embodiments described herein may be implemented in computer software using any suitable computer software language type, using, for example, conventional or object-oriented techniques. Such software may be stored on any type of suitable computer-readable medium or media, such as, for example, a magnetic or optical storage medium. The operation and behavior of the embodiments may be described without specific reference to specific software code or specialized hardware components. The absence of such specific references is feasible, because it is clearly understood that artisans of ordinary skill would be able to design software and control hardware to implement the embodiments based on the present description with no more than reasonable effort and without undue experimentation.

Moreover, the processes associated with the present embodiments may be executed by programmable equipment, such as computers or computer systems and/or processors. Software that may cause programmable equipment to execute processes may be stored in any storage device, such as, for example, a computer system (nonvolatile) memory, an optical disk, magnetic tape, or magnetic disk. Furthermore, at least some of the processes may be programmed when the computer system is manufactured or stored on various types of computer-readable media.

It can also be appreciated that certain process aspects described herein may be performed using instructions stored on a computer-readable medium or media that successful a computer system to perform the process steps. A computer-readable medium may include, for example, memory devices such as diskettes, compact discs (CDs), digital versatile discs (DVDs), optical disk drives, or hard disk drives. A computer-readable medium may also include memory storage that is physical, virtual, permanent, temporary, semi-permanent, and/or semi-temporary.

A "computer," "computer system," "host," "server," or "processor" may be, for example and without limitation, a processor, microcomputer, minicomputer, server, mainframe, laptop, personal data assistant (PDA), wireless e-mail device, cellular phone, pager, processor, fax machine, scanner, or any other programmable device configured to transmit and/or receive data over a network. Computer systems and computer-based devices disclosed herein may include memory for storing certain software modules used in obtaining, processing, and communicating information. It can be appreciated that such memory may be internal or external with respect to operation of the disclosed embodiments. The memory may also include any means for storing software, including a hard disk, an optical disk, floppy disk, ROM (read only memory), RAM (random access memory), PROM (programmable ROM), EEPROM (electrically erasable PROM) and/or other computer-readable media.

In various embodiments disclosed herein, a single component may be replaced by multiple components and multiple components may be replaced by a single component to perform a given function or functions. Except where such substitution would not be operative, such substitution is within the intended scope of the embodiments. Any servers described herein, for example, may be replaced by a "server farm" or other grouping of networked servers (such as server blades) that are located and configured for cooperative functions. It can be appreciated that a server farm may serve to distribute workload between/among individual components of the farm and may expedite computing processes by harnessing the collective and cooperative power of multiple servers. Such server farms may employ load-balancing software that accomplishes tasks such as, for example, tracking demand for processing power from different machines, prioritizing and scheduling tasks based on network demand and/or providing backup contingency in the event of component failure or reduction in operability.

The computer systems may comprise one or more processors in communication with memory (e.g., RAM or ROM) via one or more data buses. The data buses may carry electrical signals between the processor(s) and the memory. The processor and the memory may comprise electrical circuits that conduct electrical current. Charge states of various components of the circuits, such as solid state transistors of the processor(s) and/or memory circuit(s), may change during operation of the circuits.

It is to be understood that the figures and descriptions of the present invention have been simplified to illustrate elements that are relevant for a clear understanding of the present invention, while eliminating other elements, for purposes of clarity. Those of ordinary skill in the art will recognize that these and other elements may be desirable. However, because such elements are well known in the art and because they do not facilitate a better understanding of the present invention, a discussion of such elements is not provided herein.

In various embodiments disclosed herein, a single component may be replaced by multiple components and multiple components may be replaced by a single component to perform a given function or functions. Except where such substitution would not be operative, such substitution is within the intended scope of the embodiments.

While various embodiments have been described herein, it should be apparent that various modifications, alterations, and adaptations to those embodiments may occur to persons skilled in the art with attainment of at least some of the advantages. The disclosed embodiments are therefore intended to include all such modifications, alterations, and adaptations without departing from the scope of the embodiments as set forth herein.

We claim:

1. An imaging system for generating an image of a sub-surface feature of an object through a surface of the object, the system comprising:
    an illumination array, the illumination array comprising a plurality of illumination sources positioned around the sub-surface feature of the object, wherein each of the illumination sources directs illumination in an imaging wavelength range towards the surface at an angle relative to the normal of the surface;
    an imaging device comprising an objective;
    a computer system in communication with the illumination array, the computer system comprising at least one processor and operatively associated memory, wherein the computer is programmed to:
        calculate an optimized illumination pattern of the plurality of illumination sources for imaging the sub-surface feature, wherein the calculating comprises:
            receiving a first result set, wherein the first result set comprises a plurality of illumination patterns;
            for each of the plurality of illumination patterns of the first result set:
                receiving an image of the sub-surface feature of the object with the illumination pattern activated; and
                based on the image, calculating a fitness function value;
            determine that none of the fitness function values for any of the plurality of illumination patterns of the first result set exceed a threshold value; and
            generating a next result set comprising a second plurality of illumination patterns, wherein the generating is based at least in part on the first result set and the fitness function values for the plurality of illumination patterns of the first result;
        activate the optimized illumination pattern; and
        instruct the imaging device to capture an image of the sub-surface feature with the imaging device based on reflected illumination from the optimized illumination pattern.

2. The system of claim 1, wherein the object is substantially transparent over the imaging wavelength range, and wherein the object has an index of refraction that is greater than an index of refraction of a surrounding medium that surrounds the object.

3. The system of claim 1, wherein, for each of the plurality of illumination sources:
the angle is greater than an acceptance angle of an objective of an imaging device;
a first portion of the illumination is reflected at the surface and is not incident on the objective;
a second portion of the illumination is refracted through the surface towards the sub-surface feature, is incident on the sub-surface feature and is reflected by the sub-surface feature back toward the surface over a range of angles;
at least a portion of the range of angles is within an acceptance angle of the objective,
the second portion of the illumination is refracted at the surface such that an attenuated component of the second portion is refracted outside of the acceptance angle of the objective and a filtered component of the second portion is incident on the objective.

4. The system of claim 3, wherein the imaging device is configured to capture the image of the sub-surface feature based on the filtered component of the second portion received by the objective.

5. The system of claim 1, wherein calculating the optimized pattern of the plurality of illumination sources for imaging the sub-surface feature comprises applying a global search algorithm.

6. The system of claim 1, wherein calculating the optimized pattern of the plurality of illumination sources for imaging the sub-surface feature comprises applying an evolutionary algorithm.

7. The system of claim 1, wherein calculating the optimized pattern of the plurality of illumination sources for imaging the sub-surface feature comprises applying a particle swarm optimizer algorithm.

8. The system of claim 1, wherein, for at least a portion of the plurality of image patterns, the fitness function value for each of the plurality of illuminated patterns is based on a region of interest of the image.

9. The system of claim 1, wherein calculating the optimized pattern of the plurality of illumination sources for imaging the sub-surface feature comprises generating the first result set.

10. The system of claim 1, wherein calculating the fitness function value comprises measuring an, intensity contrast of the image.

11. The system of claim 1, wherein calculating the fitness function value comprises measuring a modulation contrast of a structure in the image.

12. The system of claim 1, wherein generating the next result set comprising a second plurality of illumination patterns comprises:
selecting a portion of the plurality of illumination patterns of the first result set based on the fitness function values of the plurality of illumination patterns; and
generating a plurality of child illumination patterns based on the portion of the plurality of illumination patterns, wherein the next result set comprises the plurality of child illumination patterns.

13. The system of claim 12, wherein generating the plurality of child illumination patterns comprises generating a first child illumination pattern by randomly modifying one of the portion of the plurality of illumination patterns.

14. The system of claim 12, wherein generating the plurality of child illumination patterns comprises applying a two-point cross-over operator to at least one of the portion of the plurality of illumination patterns.

15. The system of claim 12, wherein generating the plurality of child illumination patterns comprises passing at least one of the portion of the plurality of illumination patterns to the plurality of child illumination patterns.

16. The system of claim 12, wherein generating a next result set comprising a second plurality of illumination patterns comprises:
randomly assigning a velocity to each of the plurality of illumination patterns;
for each of the plurality of illumination patterns, advancing the illumination pattern one time unit based on the random velocity of the illumination pattern.

17. The system of claim 16, wherein generating a next result set comprising a second plurality of illumination patterns further comprises:
updating the velocity of at least one of the plurality of illumination patterns considering at least one of a best individual position of the at least one illumination pattern, a globally best position, a cognitive constant and a social constant.

18. The system of claim 1, wherein the calculating comprises applying a global search algorithm (GSA).

19. An imaging method for generating an image of a sub-surface feature of an object through a surface of the object, the method comprising:
calculating an optimized illumination pattern of a plurality of illumination sources for imaging the sub-surface feature, wherein the plurality of illumination sources are positioned around the sub-surface feature of the object, wherein each of the illumination sources directs illumination in an imaging wavelength range towards the surface at an angle relative to the normal of the surface for imaging the sub-surface feature, and wherein the calculating comprises:
receiving a first result set, wherein the first result set comprises a plurality of illumination patterns;
for each of the plurality of illumination patterns of the first result set:
receiving an image of the sub-surface feature of the object with the illumination pattern activated; and
based on the image, calculating a fitness function value;
determine that none of the fitness function values for the plurality of illumination patterns of the first result set exceed a threshold value; and
generating a next result set comprising a second plurality of illumination patterns, wherein the generating is based at least in part on the first result set and the fitness function values for the plurality of illumination patterns of the first result;
activating the optimized illumination pattern; and
instructing an imaging device to capture an image of the sub-surface feature with the imaging device based on reflected illumination from the optimized illumination pattern.

* * * * *